(12) United States Patent
Morein et al.

(10) Patent No.: US 12,171,828 B2
(45) Date of Patent: *Dec. 24, 2024

(54) QUIL A FRACTION WITH LOW TOXICITY AND USE THEREOF

(71) Applicant: Novavax AB, Uppsala (SE)

(72) Inventors: Bror Morein, Uppsala (SE); Karin Lövgren Bengtsson, Uppsala (SE); Jill Ekström, Uppsala (SE); Katarina Ranlund, Uppsala (SE); Kefei Hu, Uppsala (SE)

(*) Notice: Subject to any disclaimer, the term of this patent is extended or adjusted under 35 U.S.C. 154(b) by 0 days.

This patent is subject to a terminal disclaimer.

(21) Appl. No.: 18/376,666

(22) Filed: Oct. 4, 2023

(65) Prior Publication Data

US 2024/0024468 A1  Jan. 25, 2024

Related U.S. Application Data

(63) Continuation of application No. 17/477,739, filed on Sep. 17, 2021, now abandoned, which is a continuation of application No. 16/701,948, filed on Dec. 3, 2019, now abandoned, which is a continuation of application No. 15/874,262, filed on Jan. 18, 2018, now abandoned, which is a continuation of application No. 15/054,801, filed on Feb. 26, 2016, now abandoned, which is a continuation of application No. 14/714,664, filed on May 18, 2015, now abandoned, which is a continuation of application No. 14/445,690, filed on Jul. 29, 2014, now abandoned, which is a continuation of application No. 10/562,866, filed as application No. PCT/SE2004/001038 on Jul. 7, 2004, now Pat. No. 8,821,881.

(30) Foreign Application Priority Data

Jul. 7, 2003 (SE) .................................. 0301998-1

(51) Int. Cl.
*A61K 39/39* (2006.01)
*A61K 39/00* (2006.01)

(52) U.S. Cl.
CPC .... *A61K 39/39* (2013.01); *A61K 2039/55577* (2013.01); *A61K 2039/57* (2013.01)

(58) Field of Classification Search
CPC ...................................................... A61K 39/39
See application file for complete search history.

(56) References Cited

U.S. PATENT DOCUMENTS

| | | |
|---|---|---|
| 4,900,549 A | 2/1990 | De Vries et al. |
| 5,057,540 A | 10/1991 | Kensil et al. |
| 5,620,690 A | 4/1997 | Kersten et al. |
| 6,231,859 B1 | 5/2001 | Kensil |
| 6,352,697 B1 | 3/2002 | Cox et al. |
| 6,428,807 B1 | 8/2002 | MacFarlan et al. |
| 6,558,670 B1 | 5/2003 | Friede et al. |
| 8,821,881 B2 * | 9/2014 | Morein ................. A61K 39/39 424/193.1 |
| 2006/0121065 A1 | 6/2006 | Morein et al. |
| 2006/0239963 A1 | 10/2006 | Morein et al. |
| 2014/0335049 A1 | 11/2014 | Morein et al. |
| 2016/0184427 A1 | 6/2016 | Morein et al. |
| 2018/0369368 A1 | 12/2018 | Morein et al. |

FOREIGN PATENT DOCUMENTS

| | | |
|---|---|---|
| EP | 0109942 A2 | 5/1984 |
| EP | 0362279 B1 | 1/1995 |
| WO | 8809336 A1 | 12/1988 |
| WO | 9003184 A1 | 4/1990 |
| WO | 9611711 A1 | 4/1996 |
| WO | 9730728 A1 | 8/1997 |
| WO | 9836772 A1 | 8/1998 |
| WO | 2004004762 A1 | 1/2004 |
| WO | 2005002620 A1 | 1/2005 |

OTHER PUBLICATIONS

"Committee for Veterinary Medicinal Products, Quillaia Saponins, Summary Report," The European Agency fort he Evaluation of Medicinal Products, EMEA/MRL/055/95-FINAL, Feb. 1996, pp. 1-2.
Behboudi et al., "Quillaja Saponin Formulations the Stimulate . . . ," Scand. J. Immunol., 1999, vol. 50, 371-377.
Canadian Intellectual Property Office, Office Action, App. No. 2529363, Nov. 24, 2011, 2 pgs.
Canadian Intellectual Property Office, Office Action, App. No. 2529363, Oct. 18, 2010, 3 pgs.
Copland et al., "Hydration of lipid films with an aqueous solution of Quil A: a simple method for the preparation of immune-stimulating complexes," International Journal of Pharmaceutics 196:135-139 (2000).
Demana et al., "A comparison of pseudo-ternary diagrams of aqueous mixtures of Quil A, cholesterol and phospholipid prepared by lipid=film hydration and dialysis," Journal of Pharmacy and Pharmacology 56:573-580 (2004).
Demana et al., "Pseudo-ternary phase diagrams of aqueous mixtures of Quil A, cholesterol and phospholipid prepared by the lipid-film hydration method," International Journal of Pharmaceutics 270:229-239 (2004).

(Continued)

*Primary Examiner* — Albert M Navarro
(74) *Attorney, Agent, or Firm* — Carlson, Caspers, Vandenburgh & Lindquist, P.A.

(57) ABSTRACT

Fraction A of Quil A can be used together with at least one other adjuvant for the preparation of an adjuvant composition, where the included adjuvant components act synergistically to enhance level of immune response and have synergistic immunomodulating activity on the co-administered antigens or immunogens. Other adjuvants can comprise saponins, naturally occurring, synthetic or semisynthetic saponin molecules; e.g. saponins and saponin fractions from Quil A, cell wall skeleton, block polymers, TDM, lipopeptides, LPS and LPS-derivatives, Lipid A from different bacterial species and derivatives thereof, e.g., monophosphoryl lipid A, CpG variants, CT and LT or fractions thereof.

17 Claims, 21 Drawing Sheets

(56) References Cited

OTHER PUBLICATIONS

Drane, D. et al., "Iscomatrix Adjuvant for Prophylactic and Therapeutic Vaccines," Experts Rev. Vaccines, 6(5), (2007), pp. 761-772.
Ekstrom et al., "Iscom and iscom-matrix enhance by intranasal route . . . ," Vaccine, 1999, vol. 17, 2690-2701.
Ennis, FA, et al., "Augmentation of Human Influenza A Virus-Specific Cytotoxic T Lymphocyte Memory by Influenza Vaccine and Adjuvanted Carriers (ISCOMS)," Virology 259, pp. 256-261 (1999), Academic Press, Canada.
Eyles, J., et al., "Immunodominant Francisella Tularensis Antigens Identified Using Proteome Microarray," Proteomics, 2007, pp. 2172-2183.
International Search Report for PCT/SE2003/01180, dated Sep. 10, 2003.
International Search Report PCT/SE2004/001038, dated Jan. 11, 2004.
Johansson et al., "Iscoms with different quillaja saponin components . . . ," Vaccine, 1999, vol. 17, 2894-2900.
Kersten et al., "On the structure of immune-stimulating saponin-lipid complexes (iscoms)," Biochimica et Biophysica Acta, 1062:165-171 (1991).
Lavelle, E., et al., "Cholera Toxin Promotes the Induction of Regulatory T Cells Specific for Bystander Antigens by Modulating Dendritic Cell Activation," The Journal of Immunology, (2003), 171: 2384-2392.
Lovgren et al., "The Requirement of Lipids for the Formulation of Immunostimulating Complexes (Iscoms)," Biotechnol. Appl. Biochem. 10"161-172 (1988).
Lovgren-Bengtsson, K., et al., "4.5 Preparation and Use of Adjuvants," Methods in Microbiology, vol. 32, pp. 551-588 (2002), Elsevier, The Netherlands.
Morein, B., et al., "Current Status and Potential Application of ISCOMs in Veterinary Medicine," Advanced Drug Delivery Reviews, 56 (2004), pp. 1367-1382.
Nord, L., et al., "Novel Acetylated Treterpenoid Saponins in a Chromatographic Fraction form Quillaja Saponaria Molina." Carbohydrate Research 329, (2000), pp. 817-829.
Ozel et al., "Quaternary Structure of the Immunostimulating Complex (Iscom)," Journal of Ultrastructure and Molecular Structure Research 102:240-248 (1989).
Rimmelzwaan, GF et al., "A randomized, double blind study in young healthy adults comparing cell mediated and humoral immune responses induced by influenza ISCOM vaccines and conventional vaccines," Vaccine 19, pp. 1180-1187 (2001), Elsevier, The Netherlands.
Sun, H-X et al., "Advances in saponin-based adjuvants," Vaccine 27, pp. 1787-1796 (2009), Elsevier, The Netherlands.
Sun, H-X et al., "ISCOMS and ISOMATRIX," Vaccine 27, pp. 4388-4401 (2009), Elsevier, The Netherlands.
United States Patent and Trademark Office, "Final Office Action", U.S. Appl. No. 10/562,866, Dec. 1, 2009, 13 pgs.
United States Patent and Trademark Office, "Final Office Action", U.S. Appl. No. 15/874,262, Jun. 4, 2019, 7 pgs.
United States Patent and Trademark Office, "Final Office Action", U.S. Appl. No. 16/701,948, Mar. 17, 2021, 7 pgs.
United States Patent and Trademark Office, "Non-Final Office Action", U.S. Appl. No. 10/562,866, Feb. 2, 2009, 16 pgs.
United States Patent and Trademark Office, "Non-Final Office Action", U.S. Appl. No. 10/562,866, Jan. 29, 2013, 5 pgs.
United States Patent and Trademark Office, "Non-Final Office Action", U.S. Appl. No. 10/562,866, Jun. 25, 2008, 10 pgs.
United States Patent and Trademark Office, "Non-Final Office Action", U.S. Appl. No. 10/562,866, Nov. 2, 2007, 11 pgs.
United States Patent and Trademark Office, "Non-Final Office Action", U.S. Appl. No. 14/445,690, Nov. 20, 2014, 6 pgs.
United States Patent and Trademark Office, "Non-Final Office Action", U.S. Appl. No. 14/714,664, Aug. 28, 2015, 6 pgs.
United States Patent and Trademark Office, "Non-Final Office Action", U.S. Appl. No. 15/054,801, Jul. 18, 2017, 7 pgs.
United States Patent and Trademark Office, "Non-Final Office Action", U.S. Appl. No. 15/054,801, Nov. 28, 2016, 7 pgs.
United States Patent and Trademark Office, "Non-Final Office Action", U.S. Appl. No. 15/874,262, Nov. 13, 2018, 7 pgs.
United States Patent and Trademark Office, "Non-Final Office Action", U.S. Appl. No. 16/701,948, Aug. 26, 2020, 10 pgs.
United States Patent and Trademark Office, "Non-Final Office Action", U.S. Appl. No. 17/477,739, Apr. 5, 2023, 8 pgs.
Written Opinion of ISA for PCT/SE2004/001038, 6 pages, dated Nov. 1, 2004.
Written Opinion of ISA PCT/SE2004/001038, dated Jan. 11, 2004.

* cited by examiner

| group | QWT-matrix | QHC-matrix |
|---|---|---|
| 1 | 50 µg | 0 |
| 2 | 0 | 50 µg |

Group 1) 5 ug OVA

Group 2) 5 ug OVA +
QWT-Matrix (6 ug)

Group 3) 5 ug OVA +
QHC-Matrix (6 ug)

Group 4) 5 ug OVA +
QWT-Matrix (6 ug)
QHC- Matrix (2 ug)

A

B

A

B

QUIL A FRACTION WITH LOW TOXICITY AND USE THEREOF

CROSS-REFERENCE TO RELATED APPLICATIONS

This application is a continuation of application Ser. No. 17/477,739, filed Sep. 17, 2021, which is a continuation of application Ser. No. 16/701,948, filed Dec. 3, 2019, now abandoned, which is a continuation of application Ser. No. 15/874,262, filed Jan. 18, 2018, now abandoned, which is a continuation of application Ser. No. 15/054,801, filed Feb. 26, 2016, now abandoned, which is a continuation of application Ser. No. 14/714,664, filed May 18, 2015, now abandoned, which is a continuation of application Ser. No. 14/445,690, filed Jul. 29, 2014, now abandoned, which is a continuation of application Ser. No. 10/562,866, filed May 16, 2006, now U.S. Pat. No. 8,821,881, which is a national stage application of International Appl. PCT/SE04/01038, filed Jul. 7, 2004 and which claims priority of Swedish patent Appl. No. 0301998-1, filed Jul. 7, 2003, all of which are hereby incorporated by reference.

FIELD OF INVENTION

The present invention relates to the use of fraction A of Quil A together with at least one other adjuvant for the preparation of an adjuvant composition with synergistic effects including level of immune responses and immunomodulating activity.

PRIOR ART

There is a great need for efficient adjuvant and vaccine delivery systems both for man and animal to be used for immune prophylactics or for immune therapy. For animal vaccines there are a number of different adjuvants including iscom and iscom matrix adjuvanted vaccines. However, only aluminium hydroxide and calcium phosphate adjuvants are commercially available in human vaccines, and an oil emulsion adjuvant (MF59) has recently been registered for a human influenza vaccine. Thus, there is a lack of efficient adjuvants, particularly for human vaccines. Adjuvants are not only important for enhancing the level immune response but even more for the quality or type of immune response, which has to match the type of infection the vaccine is intended to protect against. With regard to pathogens establishing themselves intracellularly like viruses, but also some bacteria and parasites, a so-called Th1 type of immune response is required for optimal immune protection, and in many cases a Th1 type of response is a prerequisite for immune protection. However, it is also now well established, that a pure Th1 or Th2 type of response may cause side effects, since a balance between the two types of the T helper cells are required for immune regulation. I.e. the Th1 response regulate the Th2 response e.g. by the production of IFN-γ and the Th1 response is regulated by the Th2 response e.g. by the production of the cytokine IL10. Thus, the Th1-Th2 balance is essential to avoid side effects. To be able to induce correct type of immune response for protection against the various pathogens a number of adjuvants will be required. A Th1 response is reflected by the IgG2a antibody response, and therefore used as a marker for Th1 t helper cell response. One important aspect for adjuvants is the safety including the fact that the immune response evoked shall have a quality to avoid side effects when a subsequent infection occurs after the vaccination. Severe side effects were the case with respiratory syncytial virus when an aluminium hydroxide adjuvanted formalin inactivated respiratory syncytial virus (RSV) vaccine was tried in children nearly 30 years ago. The vaccinated children became sicker and there was a higher death rate among them after natural infection with RSV than in non-vaccinated children.

Acute toxicity or side effects have been major concerns for both veterinary and particularly human use of quillaja saponins in vaccine preparations. Theses goals were only partially met with success, the purified fractions e.g., QA-21 (EP 0 362 279 B2) and combinations of fractions A and C (WO 96/11711, Iscotec-patent) were indeed chemically defined compared to "*Quillaja saponaria* Molina" but they still caused some toxicity and side effects.

It has now turned out that fraction A of Quil A has a low toxicity, and in low dose enhance and the level of immune responses and the immunomodulatory capacity of other adjuvants in suboptimal doses, which when used by themselves may be toxic or cause side-effects in efficient doses. Thus, it facilitates the use of other adjuvants which, when used by themselves, might be toxic in doses they are efficient.

SUMMARY OF INVENTION

The present invention relates to the use of fraction A of Quil A together with at least one other adjuvant for the preparation of an adjuvant composition with synergistic effect to enhance the level of immune responses and immunomodulating activity. It especially concerns the use of fraction A of Quil A in a composition comprising iscom particles wherein the different fractions of Quil A are integrated into different iscom and iscom matrix particles.

Figure 1:
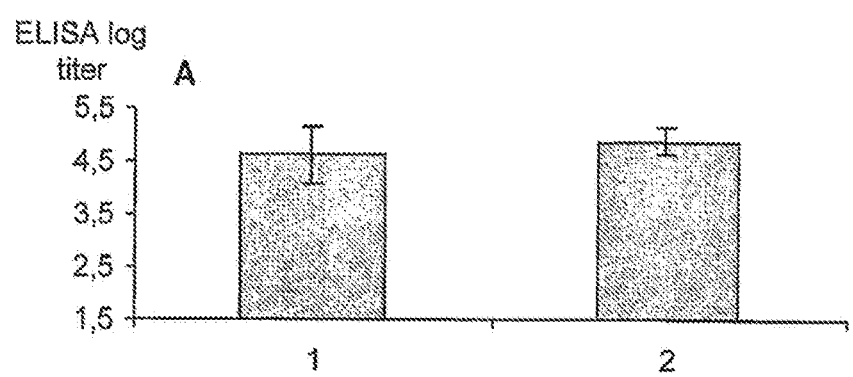
FIG. 1
Figure 1:
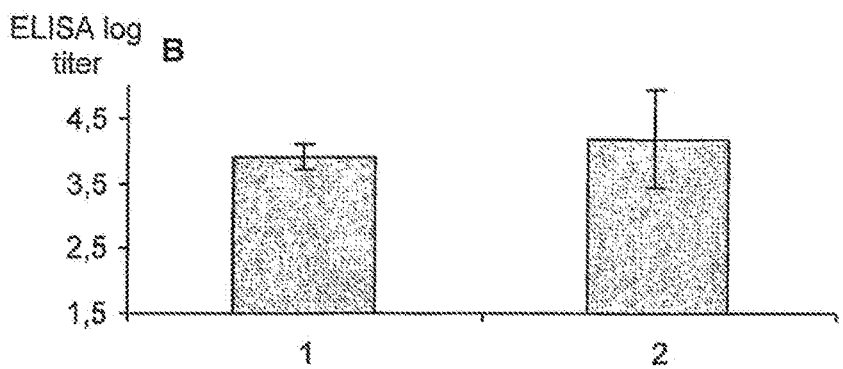

High dose (50 µg) of QHC in matrix is toxic, while a high dose of QWT in matrix is non-toxic when supplemented to OVA to enhance the antibody response in Balb/C mice (see text). Both formulations enhance similar specific antibody responses against OVA as measured 3 weeks after the second immunisation by ELISA for the total IgG response (A) and in the IgG2a subclass (B).

FIG. 2

Synergistic effects of QWT-matrix and QHC-matrix when supplemented to OVA to enhance the antibody response in Balb/C mice (see text). The dose of QWT-matrix and QHC-matrix ranged as follows in group 1, no QWT or C; Gr. 2, 0.3 µg QWT no C; Gr. 3, 0.3 µg QWT+2 µg C; Gr. 4, 10 µg QWT no C; Gr. 5, 10 µg QWT 2 µg C. The dose of OVA was 10 µg. There were 8 mice per group, which were immunised twice 4 weeks apart s.c. with respective formulation. The antibody titres were measured by ELISA against OVA:

A Total IgG 3 weeks after the first immunization.
B IgG2a 2 weeks after the second immunization.
C IgG1 2 weeks after the second immunization.

FIG. 3

Toxicity of QWT and AC (i.e. 703) respiratory syncytial virus (RSV) iscoms measured by survival rate in newborns (1 week old) mice after one intraperitoneal injection with 1 µg iscom (protein). The protein/saponin ratio is 1/1.

FIG. 4

Antibody response of newborn (1 week old) and adult mice after one intraperitoneal immunisation and a subsequent boost after 3 weeks with 1 µg iscom (protein). The protein/saponin ratio is 1/1.

FIG. 5

Cytotoxic T cell (CTL) response after one intraperitoneal immunisation with 1 µg iscom (protein). The protein/saponin ratio is 1/1. The spleen cells were collected 1 and 3 weeks after the intraperitoneal immunization.

FIG. 6

QWT matrix is less toxic on VERO cells (a monkey cell line) than 703 matrix and C matrix after exposure for 72 hrs in culture measured by growth rate proportional (%) to non-exposed cell cultures. QWT matrix is well tolerated at all concentrations tested i.e. up to 1300 µg. No cell growth is recorded in cell cultures exposed 800 µg of 703 matrix or 45 µg of QHC matrix.

A. Exposure of VERO cells to QWT matrix and 703 matrix as indicated.
B. Exposure of VERO cells to QHC matrix as indicated.

FIG. 7

QWT matrix is less toxic on spleen cells obtained from mice than C matrix after exposure for 72 hrs in culture measured by growth rate measured by a colorimetric method as described in the text. The growth rate is compared with spleen cells grown in medium alone or together with mitogen Con A.

A. Exposure of spleen cells to QWT matrix in decreasing doses from 10 to 1.25 µg as indicated.
B. Exposure of spleen cells to QHC matrix in decreasing doses from 10 to 1.25 µg as indicated.

FIG. 8

This figure shows the preparation of fractions A, B and C by HPLC;

FIG. 9

This figure shows synergistic effect of QWT-matrix and QHC-matrix. Groups of 8 female Balb/c mice were immunised s.c. at the base of the tail with 5 micrograms of ovalbumin (OVA) alone (Gr 1) or mixed with A-matrix (Gr 2) or C-matrix (Gr 3) respectively or a mixture of A-matrix and C-matrix (Gr 4). The mice were immunised at weeks 0 and 4, serum samples were taken at weeks 3 (prime) and 6 (booster). The sera were tested for antigen specific antibodies IgG or subclasses (IgG 1 and IgG2a) in ELISA. The antibody response to OVA (5 µg) is strongly enhanced by a combination of QWT-Matrix and QHC-Matrix compared to the use of either Matrix on its own. Particularly the IgG2a response is enhanced. The enhancement (IgG and IgG2a) is demonstrated three weeks after priming (A and B).

FIG. 10

Figure 9:
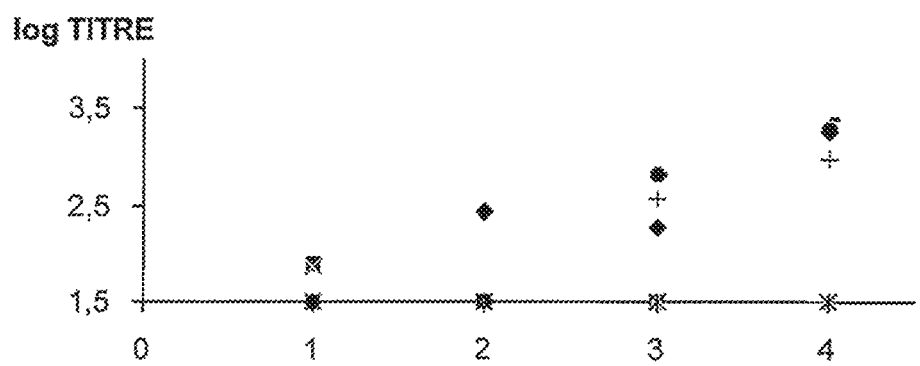
Figure 9:
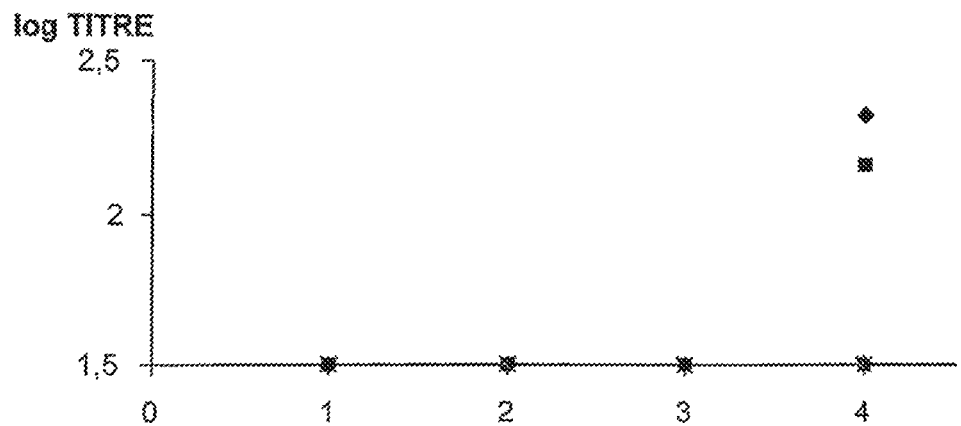

With reference to FIG. 9, the enhancement of IgG also is shown two weeks after booster.

FIG. 11

With reference to FIG. 9, the enhancement of IgG1 also is shown two weeks after booster.

FIG. 12

With reference to FIG. 9, the enhancement of IgG2a also is shown two weeks after booster.

FIG. 13

This figure shows antibody responses (total IgG and IgG2a) to OVA after immunization with 5 mg of OVA alone (Gr 1) or mixed with QWT (Gr2) or mixed with a combination of QWT and CT (Gr 3) or QWT and MPL (Gr 4) respectively. The synergistic adjuvant effect of QWT-Matrix given together with CT or MPL is demonstrated for a week immunogen; OVA. Both the magnitude of the IgG response (A) and particularly a specific enhancement (immunomodulation) of the IgG2a subclass (B) should be noted.

FIG. 14

This figure shows antibody response (total IgG) to TT (Tetanus Toxoid) after immunization with 2.5 Lf of TT alone or with CT (1 or 0.2 µg) or a combination of QWT and 0.2 µg of CT after first immunization.

FIG. 15

Figure 14:
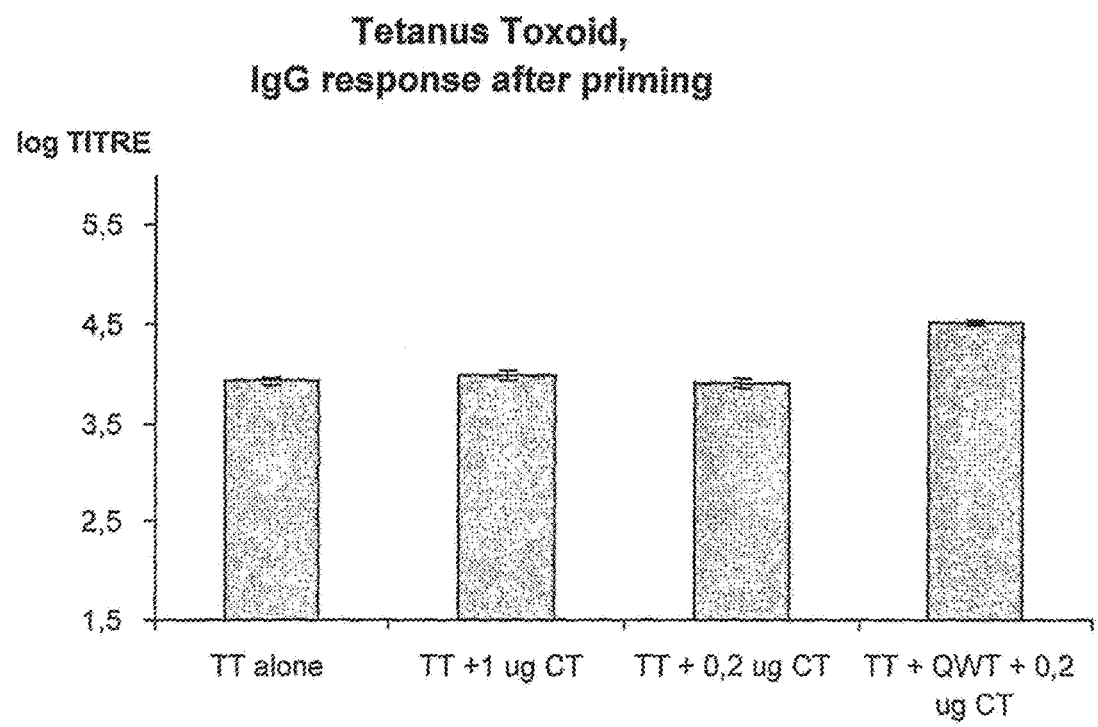

With reference to FIG. 14, antibody response (total IgG) also is shown after booster.

FIG. 16

This figure shows antibody response (IgG2A) to TT (Tetanus Toxoid) after immunization with 2.5 Lf of TT alone or with CT (1 or 0.2 µg) or a combination of QWT and 0.2 µg of CT after first immunization.

FIG. 17

Figure 16:
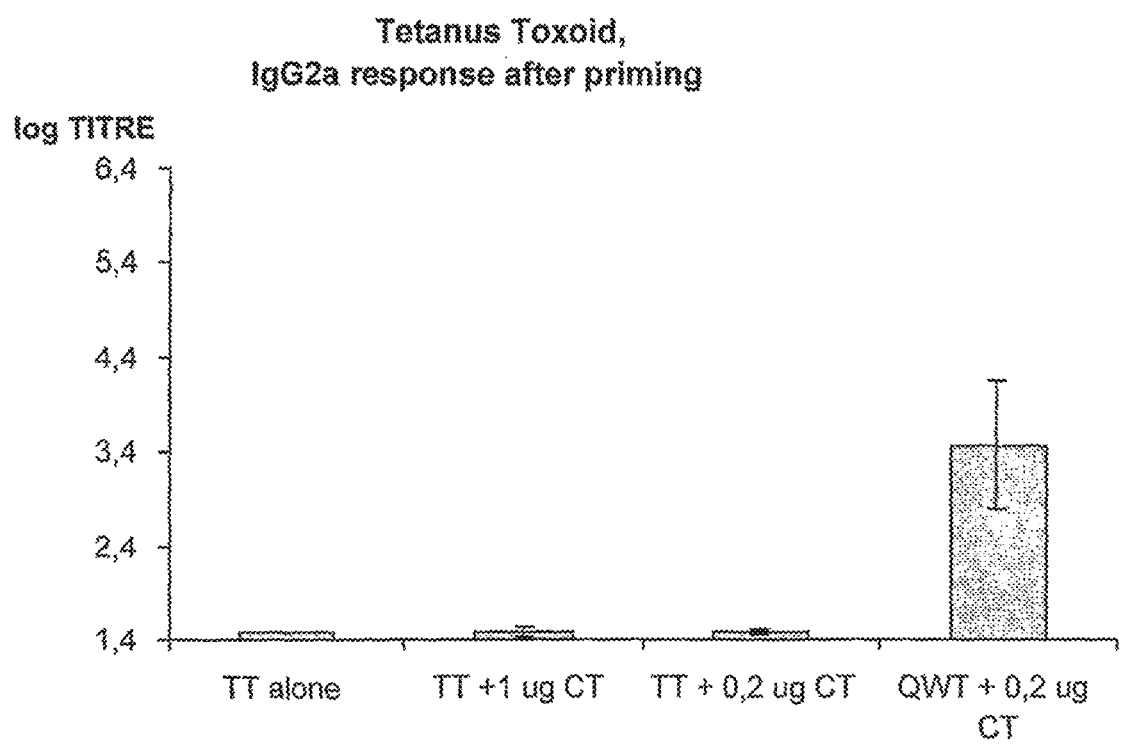

With reference to FIG. 16, antibody response (IgG2A) also is shown after booster.

Figure 15:
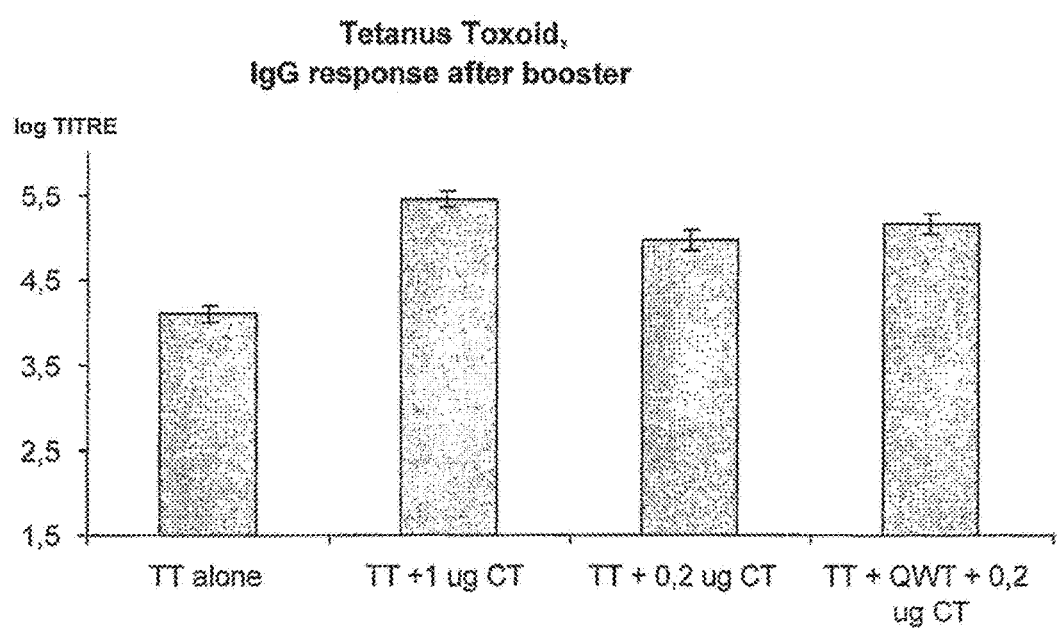

Antibody response to TT (Tetanus Toxoid) is enhanced and modulated by addition of QWT-Matrix. The IgG response after addition of QWT-Matrix to a low dose of CT (0.2 µg) is in the same range as that of 1 µg of CT (FIG. 14 and FIG. 15). The IgG2a response (FIG. 16 and FIG. 17) is however strongly enhanced, indicating a synergistic modulatory effect of QWT-Matrix and CT.

FIG. 18

This figure shows antibody response (total IgG) to TT (Tetanus Toxoid) after immunization with 2.5 Lf of TT alone or with MPL (50 or 10 µg) or a combination of QWT and 10 µg MPL after first immunization.

FIG. 19

Figure 18:
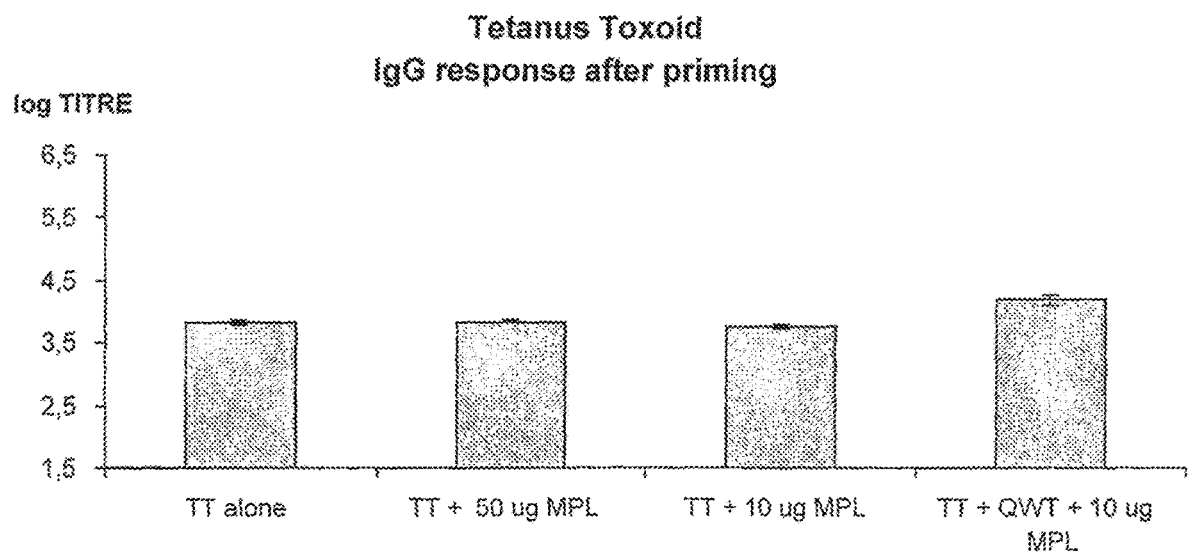

With reference to FIG. 18, antibody response (total IgG) to TT (Tetanus Toxoid) also is shown after booster.

FIG. 20

This figure shows antibody response (IgG2a) to TT (Tetanus Toxoid) after immunization with 2.5 Lf of TT alone or with MPL (50 or 10 µg) or a combination of QWT and 10 µg MPL after first immunization.

FIG. 21

Figure 20:
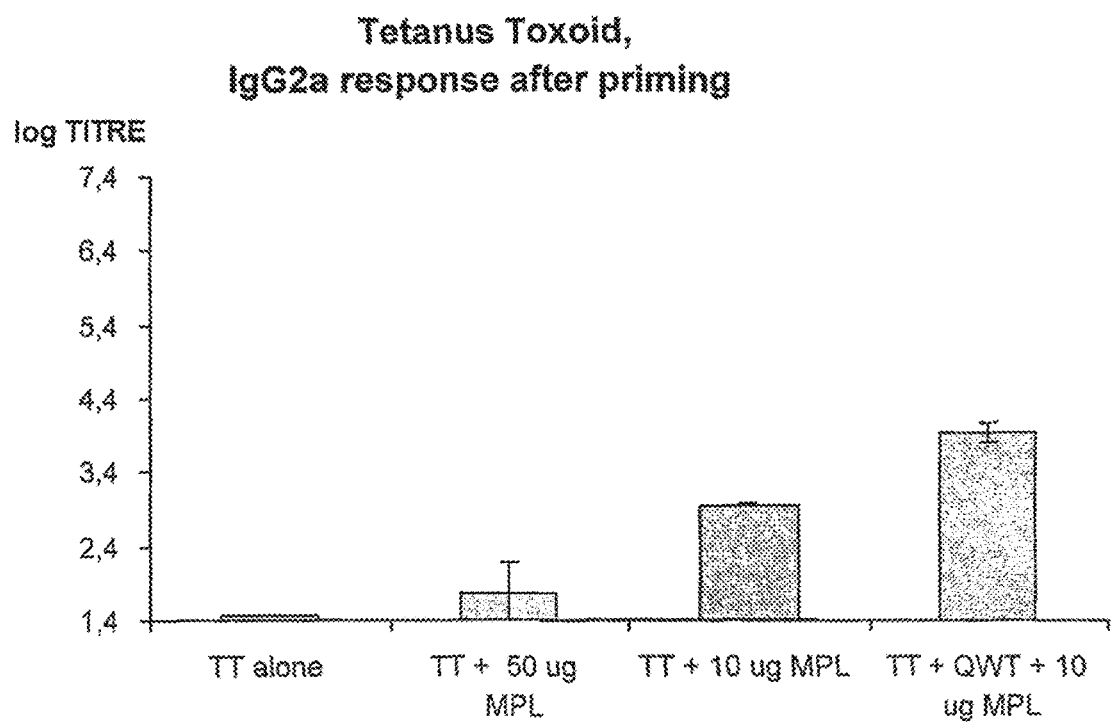

With reference to FIG. 20, antibody response (IgG2a) to TT (Tetanus Toxoid) also is shown after booster.

Figure 19:
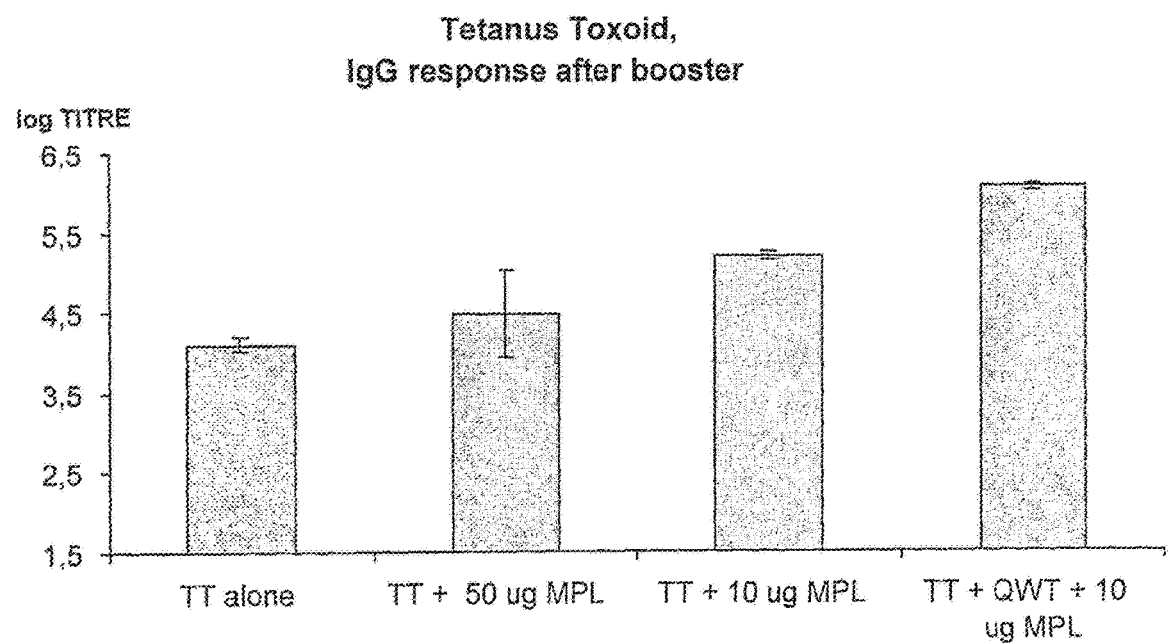

The adjuvant effect of Monophosphoryl Lipid A (MPL), measured as antibody response to Tetanus Toxoid (TT), is enhanced and modulated by addition of QWT-Matrix. The IgG response after addition of QWT-Matrix to a low dose of MPL (10 µg) higher than that of both 50 and 10 µg of MPL (FIG. 18 and FIG. 19). The IgG2a response (FIG. 20 and FIG. 21) is strongly enhanced, indicating a synergistic modulatory effect of QWT-Matrix and MPL.

DETAILED DESCRIPTION OF THE INVENTION

The invention relates to the use of fraction A of Quil A together with at least one other adjuvant for the preparation of an adjuvant composition with synergistic effect to enhance the level and quality immunomodulating activity. It especially relates to the use of fraction A of Quil A together with one or more other adjuvants where fraction A at a low and well tolerated dose synergistically enhance the immuno enhancing effect of the co administered adjuvant, which by its own is too toxic for prophylactic or clinical use. I.e. a low well tolerated (otherwise suboptimal) dose of the co-administered adjuvant is rendered efficient and feasible for use. Thus, the other adjuvants are preferably those, which have a substantial toxicity and the dose of which has to be lowered to be accepted for prophylactic and clinical use, but also adjuvants which are weak and cannot by their own enhance efficient levels of immune responses or exert efficient qualitative immunomodulating capacity.

The at least one other adjuvant may be chosen preferably from saponins, naturally occurring, or derivatives thereof, synthetic or semi synthetic saponin molecules derived from crude saponin extract of *Quillaja saponaria* Molina; e.g. saponins and saponin fractions from Quil A, cell wall skeleton, blockpolymers, e.g. hydrophilic block copolymers, e.g. CRL-1005, TDM (Threhalose di mucolate), lipopeptides, LPS and LPS-derivatives, Lipid A from different bacterial species and derivatives thereof, e.g., monophosphoryl lipid A, muramyl di or tripeptide or derivatives thereof, CpG variants, CpGODN variants, endogenous human animal immunomodulators, e.g. GM-CSF, IL-2, adjuvant active bacterial toxins, native or modified, e.g. cholera toxin CT, and its subcomponents CTB and CTA1, thereto labile toxin (LT) of *E. coli*, or *Bordetella pertussis* (BP) toxin and the filamentus heamagglutenin of BP.

The saponin fractions from Quil A other than fraction A may be the B and C fractions described in WO 96/11711, the B3, B4 and B4b fractions described in EP 0 436 620. The fractions QA1-22 described in EP 0 362 279 B2, Q-VAC (Nor-Feed, AS Denmark), *Quillaja saponaria* Molina Spikoside (Isconova AB, Uppsala Science Park, 75183 Uppsala, Sweden).

The fractions QA-1-2-3-4-5-6-7-8-9-10-11-12-13-14-15-16-17-18-19-20-21 and 22 of EP 0 362 279 B2, Especially QA-7, 17-18 and 21 may be used. They are obtained as described in EP 0 362 279 B2, especially at page 6 and in Example 1 on page 8 and 9.

Fractions A, B and C described in WO 96/11711 are prepared from the lipophilic fraction obtained on chromatographic separation of the crude aqueous *Quillaja saponaria* Molina extract and elution with 70% acetonitrile in water to recover the lipophilic fraction. This lipophilic fraction is then separated by semipreparative HPLC with elution using a gradient of from 25% to 60% acetonitrile in acidic water. The fraction referred to herein as "Fraction A" or "QH-A" is, or corresponds to, the fraction, which is eluted at approximately 39% acetonitrile. The fraction referred to herein as "Fraction-B" or "QH-B" is, or corresponds to, the fraction, which is eluted at approximately 47% acetonitrile. The fraction referred to herein as "Fraction C" or "QH-C" is, or corresponds to, the fraction, which is eluted at approximately 49% acetonitrile.

Preferably the at least other adjuvant is sub fragment C or B from Quil A.

In one embodiment of the invention the adjuvant fraction A of Quil A, in this text also referred to as QWT and the at least one other adjuvant may be integrated into each one different iscom particle or iscom matrix particles. They may also be integrated into one and the same iscom particle or iscom matrix particles. Thus the adjuvants may be integrated into each a different iscom particle or different iscom matrix particles and then mixed in a composition.

The iscom particle may be an iscom complex or an iscom matrix complex made from any saponin. The adjuvant fraction A and the other at least one adjuvant may also be coupled on to the different or the same iscom particles or iscom matrix particles or one or more of the adjuvants may be mixed with the iscom particles.

In order to be integrated into iscom particles the adjuvants need to have some hydrophobic molecule. Adjuvants that do not have hydrophobic molecules may be coupled to such molecules. Hydrophobic molecules and coupling methods are described in EP 180564. Preferably the adjuvants are integrated into different iscom particles.

In another embodiment of the invention the adjuvant fraction A of Quil A is integrated into iscom particles, whereas the other at least one adjuvant are not integrated into iscom particles and are used in free form in the composition.

In another preferred embodiment of the invention the adjuvant fractions of Quil A is integrated into iscom particles or iscom matrix particles, whereas other adjuvants are not integrated into iscom particles or iscom matrix particles and are used in free form in the composition.

In another especially preferred embodiment the composition comprises fraction A of Quit A integrated into iscom particles or is corn matrix particles and at least one other adjuvant, which is not integrated into iscom particles or iscom matrix particles.

In another preferred embodiment the at least other adjuvant is MPL or cholera toxin CT. The MPL or cholera toxin may be integrated into the same iscom particle or iscom matrix particle or into each a different iscom particle or iscom matrix particle. Preferably the MPL or cholera toxins are in free form.

In still another preferred embodiment the Quil A fraction A is incorporated into an iscom particle or iscom matrix particle and the at least one other adjuvant is incorporated into each a different iscom particle or iscom matrix particle or the other at least on other adjuvant is incorporated into the same iscom or iscom matrix particle but different form the particle into which the Quil A fraction A was incorporated or the other at least one adjuvant is in free form.

The adjuvant fraction A and the other (co-administered) at least one adjuvant may also be formulated in liposomes or with oil-based adjuvant formulation or with a non-ionic block polymer or presented in another particulate formulations such as PLG, starch, Al(OH)3 or in free form.

Iscom contains at least one glycoside, at least one lipid and at least one type of antigen substance. The lipid is at least a sterol such as cholesterol and optionally also phosphatidyl choline. These complexes may also contain one or more other immunomodulatory (adjuvant-active) substances, and may be produced as described in EP 0 109 942 B1, EP 0 242 380 B1 and EP 0 180 564 B1.

An iscom matrix comprises at least one glycoside and at least one lipid. The lipid is at least a sterol such as cholesterol and optionally also phosphatidyl choline. The iscom complexes may also contain one or more other immunomodulatory (adjuvant-active) substances, not necessarily a saponin, and may be produced as described in EP 0 436 620 B1.

In a preferred formulation iscoms and iscom matrix have been formulated with fraction A and C of Quillaja in different iscom particles, which cause minimal side effects (see the examples). These iscoms have been compared with a formulation comprising 70% of fraction A and 30% of fraction. C of Quil A called 703 and produced according to WO 96/11711, which is in clinical trial in man for a human influenza virus vaccine. According to WO 96/11711 the A and C fractions are integrated into the same particle. The toxicity study was carried out in newborn mice, which are much more sensitive than adult mice. The study shows that the newborn mice better tolerate the new iscoms produced from fraction A of Quil A than the 703 formulation. Furthermore, the efficacy of the new formulations according to the invention is tested with antigens from a pathogen i.e. human respiratory syncytial virus hRSV and with a weak antigen i.e. ovalbumin (OVA). A synergistic effect of fraction A of Quil A in a matrix formulation named QWT is shown in example 1. Also strong antigens like cholera toxin (CT) and tetanus toxin can be modulated by the adjuvant formulations according to the present invention by enhancing antibody increase, but above all by potent immuno modulation as described in examples 8 and 9.

A composition according to the invention may comprise the adjuvant fraction A from Quit A and the at least one other adjuvant in any weight ratios. Preferably fraction A of Quil A is from 2-99.9 weight %, preferably 5-90 weight % and especially 50-90 weight % counted on the total amount of adjuvants. For e.g. Al(OH)3, oil adjuvants and block polymers the amount of fraction A, of Quil A may be substantially lower.

One preferred iscom composition comprises 50-99.9% of fragment A of Quil A and 0.1-50% of fragment C and/or fraction B and/or other fractions or derivatives of Quit A (hereinafter non-A Quil A fractions) counted on the total weight of fractions A and non-A Quil A fractions. Especially the composition comprises 70-99.9% of fragment A of Quil A and 0.1-30% of non-A Quil A fractions, preferably 75-99.9% of fragment A of Quil A and 0.1-25% of non-A Quil A fractions and especially 80-99.9% of fragment A of Quit A and 0.1-20% of non-A Quil A fractions counted on the total weight of fraction A and non-A Quil A fractions. Most preferred composition comprises 91-99.1% of fragment A of Quil A and 0.1-9% of non-A Quil A fractions counted on the total weight of fractions A and non-A Quil A fractions, especially 98.0 99.9% of fraction A and 0.1-2.0% of non-A Quit A fractions counted on the total weight of fractions A and non-A Quil A fractions.

The composition may further comprise a pharmaceutically acceptable carrier, diluent, excipient or additive.

For the purposes of identification of Fractions A, B and C referred to herein, reference may be made to the purification procedure of Example 1. In general terms, in this procedure Fractions A, B and C are prepared from the lipophilic fraction obtained on chromatographic separation of the crude aqueous Quil A extract and elution with 70% acetonitrile in water to recover the lipophilic fraction. This lipophilic fraction is then separated by semipreparative HPLC with elution using a gradient of from 25% to 60% acetonitrile in acidic water. The fraction referred to herein as "Fraction A" or "QH-A" is, or corresponds to the fraction, which is eluted at approximately 39% acetonitrile. The fraction referred to herein as "Fraction B" or "QH-B" is, or corresponds to, the fraction, which is eluted at approximately 47% acetonitrile. The fraction referred to herein as "Fraction C" or "QH-C" is, or corresponds to, the fraction, which is eluted at approximately 49% acetonitrile.

When prepared as described herein, Fractions A, B and C of Quil A each represent groups or families of chemically closely related molecules with definable properties. The chromatographic conditions under which they are obtained are such that the batch-to-batch reproducibility in terms of elution profile and biological activity is highly consistent.

All publications mentioned herein are incorporated by reference. By the expression "comprising" we understand including but not limited to. The invention will now be described by the following non-limiting examples. The scope of the invention is rather what the skilled person would interpret from the disclosure and found equivalent or a natural development thereof.

Example 1

In this experiment it is emphasised that QWT in iscom and matrix is well tolerated and has a strong immune enhancing and immune modulatory capacity. Ovalbumin (OVA) is used because it is a weak antigen and as such it does not induce a Th1 type of response. QWT is compared with QHC, since it is evaluated in human clinical trials.

Materials and Methods

Formulation of OYC, QWT and 703-Matrix Iscoms

A mixture of phosphatidyl choline (PC) and cholesterol (C) (15 mg/ml of each) is prepared in 20% MEGA-10 in water. The preparation is heated to 60° C. and treated with light sonication until all lipid is solubilised.

Quillaja saponin is dissolved to 100 mg/ml in water. The 703 mixture contains 7 parts (by weight) of Fraction A and 3 parts of Fraction C.

QWT saponin contains Fraction A alone.

703-matrix. 5 ml of PBS is mixed with 10 mg of the PC/C mixture (667 microliters), 35 mg 703 (350 microliters) is added, the mixture is mixed and PBS is added to a final total volume of 10 ml. The mixture is extensively dialysed against PBS using a Slide-A-Lyser (3-15 ml, Pierce) dialysis cassette.

QWT-matrix, and QHC-matrix 5 ml of PBS is mixed with 10 mg of each PC and C (667 microliters), 40 mg QWT (400 microliters) and 30 mg of QHC (300 microliters) respectively is added, the mixture is mixed and PBS is added to a final total volume of ml. The mixture is extensively dialysed against PBS using a Slide-A-Lyser (3-15 ml, Pierce) dialysis cassette.

Experimental Design

Female MNRI mice (18-20 g) were used in this Example. Group 1 consisted of 8 mice immunised twice 4 weeks apart subcutaneously (s.c.) with 10 µg OVA adjuvanted with 50 µg QWT matrix. Group 2 had the same number of mice immunised by the same procedure but the adjuvant was 50 µg QHC matrix. Sera were collected before first immunisation and 3 weeks after and 2 weeks after the boost.

Antibody Determination

The specific OVA serum antibody responses were determined by ELISA both for total IgG response (including all IgG subclasses) and in the IgG2a subclasses as described before (Johansson, M and Lövgren-Bengtsson (1999) Iscoms with different quillaja saponin components differ in their immunomodulating activities. Vaccine 19, 2894-2900).

Results

All mice immunised with OVA adjuvanted with QWT matrix survived and did not develop any sign of discomfort. Out of 8 mice immunised with OVA adjuvanted with QHC matrix 4 mice (50%) died.

There is no significant difference between the groups with regard total antibody responses (FIG. 1(A)), but there is more spread of the antibody titres between the animals in group 1, i.e. mice immunised with OVA adjuvanted with QWT-matrix.

There was no difference in mean titres in the IgG2a subclass between group 1 and 2 (FIG. 1(B)), but there is more spread of the antibody titres between the animals in group 2, i.e. mice immunised with OVA adjuvanted with QHC-matrix.

Figure 2:
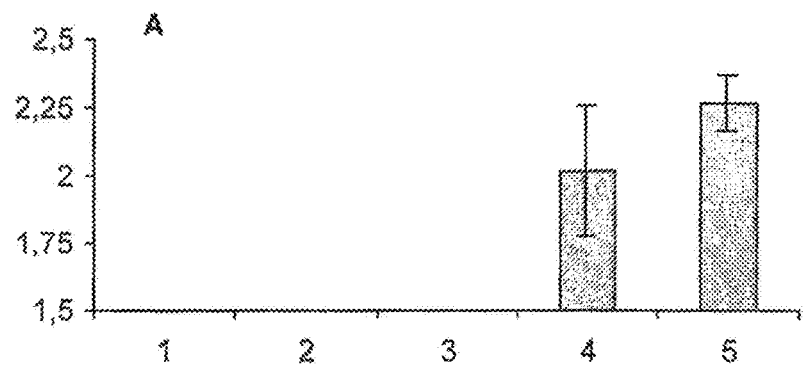
Figure 2:
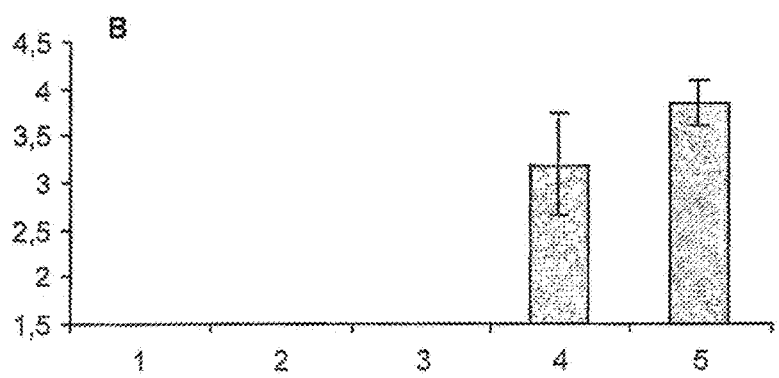
Figure 2:
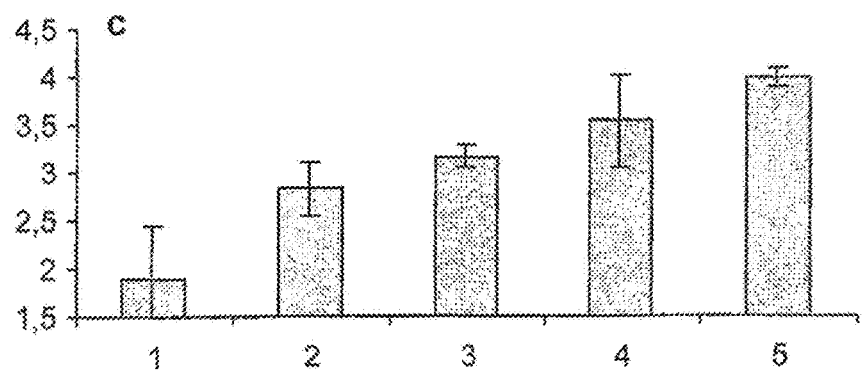

In the second experiment of this example it was explored whether QWT matrix can benefit from the complementation of another adjuvant, or it facilitate the use of a more toxic adjuvant. The IgG2a response reflects that the Th2 type of lymphocytes are involved. The dose of QWT-matrix and QHC-matrix ranged as follows; in group 1, no QWT-matrix or QHC-matrix; Gr. 2, 0.3 µg QWT-matrix no QHC-matrix; Gr. 3, 0.3 µg QWT-matrix+2 µg QHC matrix; Gr. 4, 10 µg QWT-matrix no QHC; Gr. 5, 10 µg QWT-matrix+2 µg QHC-matrix X. The dose of OVA was 10 µg. There were 8 mice per group, which were immunised twice 4 weeks apart s.c. with respective formulation. (example 8 FIGS. 2(A), (B) and (C)).

Sera were collected 3 weeks after the first immunisation and 2 weeks after the boost.

The OVA specific serum antibody responses were determined by ELISA for total IgG response and in the IgG2a and IgG1 subclasses as described (Johansson, M and Lövgren-Bengtsson (1999). Iscoms with different quillaja saponin components differ in their immunomodulating activities. Vaccine 19, 2894-2900).

Results

After the first immunisation no antibody response was recorded in mice receiving non-adjuvanted OVA or OVA adjuvanted with 0.3 μg of QWT matrix with and without 2 μg of QHC matrix (FIG. 2(A)).

After the second immunisation a low response was detected in 3 out of 8 mice immunised with non-adjuvanted OVA in the IgG1 subclass (FIG. 2(B)), but no response was recorded in the IgG2a subclass. Neither was antibody responses recorded in the IgG2a subclass with the lowest adjuvant doses of QWT matrix i.e. 0.3 μg with and without 2 μg of QHC matrix (FIG. 2(B)). There was a clear enhancement of the antibody response in the IgG2a subclass, when the low dose of 2 μg QHC matrix was added to the 10 μg of QWT matrix (FIG. 2(B)).

Conclusion

QWT has a low toxicity and still a strong modulatory effect as shown by promoting a strong TH1 type of response, in contrast to the non-adjuvanted or the very low adjuvanted OVA, which only elicited antibody response in the IgG1 subclass. It is also shown that the QWT matrix synergies with a low dose of QHC matrix. This fact is important, because QWT makes it possible to optimise the adjuvant effect and minimise the side effects of other adjuvants.

Example 2

Respiratory syncytial virus (RSV) is a major pathogen for young children (hRSV) but also for elderly. A closely related virus (bRSV) is a pathogen for young calves causing severe disease and high economical losses for calf breeders. The envelope proteins of hRSV were selected as model antigens, because they represent antigens from a pathogen for which a vaccine is lacking and for which there is a great need. The newborn mouse represents a model for the newborn, and a very sensitive animal, which requires a vaccine formulation virtually free of side effects, and a model in which important immunological reactions can be measured because of available reagents techniques. An early vaccine against hRSV was tested in children, but it did not protect against disease. On the contrary it exacerbated disease when a subsequent natural infection occurred. In this experiment we have selected 703 as a quillaja component in the ISCOM to compare with the present invention, because a 703 vaccine formulation is in human trials, thus a candidate for human vaccines. In the present experiment the toxicity of QWT iscoms and 703 iscoms is compared.

Materials and Methods

Formulation of 703 and QWT RSV-ISCOMs

RSV iscoms with different Quillaja saponin compositions (A, C and AC i.e., ISCOPREP™703) were prepared from sucrose gradient purified HRSV, essentially using the method described previously [17,18]. Briefly, 2 ml (1.6 mg/ml) purified RSV was solubilized with OG (1-O-n-Octyl-β-D-glueopyranosid, C14H2806, Boehringer, Mannheim, GmbH, FRG) at a final concentration of 2% (w/v) for 1 h at 37° C. under constant agitation. The solubilized virus was applied onto a discontinuous sucrose gradient of 2 ml 20% sucrose layer containing 0.5% OG, over a cushion of 50% sucrose. After centrifugation at 210,000 g at 4° C. in a Kontron TST-41 rotor for 1 h, the sample volume together with the 20% sucrose layer containing viral proteins were collected, and extra lipids I.e. cholesterol and phosphatidylcholine, and Quillaja saponin, i.e. QH-A or QH-C or ISCOPREP™703 was added in proportions of protein:cholesterol:phosphatidylcholine:Quillaja saponin=1:1:1:5 calculated by weight. After extensive dialysis against 0.15 M ammonium acetate at 4° C. for 72 h, the ISCOMs were purified by centrifugation through 10% sucrose at 210,000 g in Kontron TST-41 rotor at 10° C. for 18 h. The pellet containing the iscoms was re-suspended in 200 μl PBS. Protein concentration was determined by amino acid analysis (Aminosyraanalyslaboratoriet, Uppsala, Sweden). Samples were submitted for negative staining electron microscopy. No morphological differences were observed among the three iscoms. All showed typical iscom structures, i.e. cage-like spherical particles with a diameter of around 40 nm. The RSV antigens and iscom structures were found in the same fraction of a sucrose gradient after centrifugation.

Experimental Design

Figure 3:
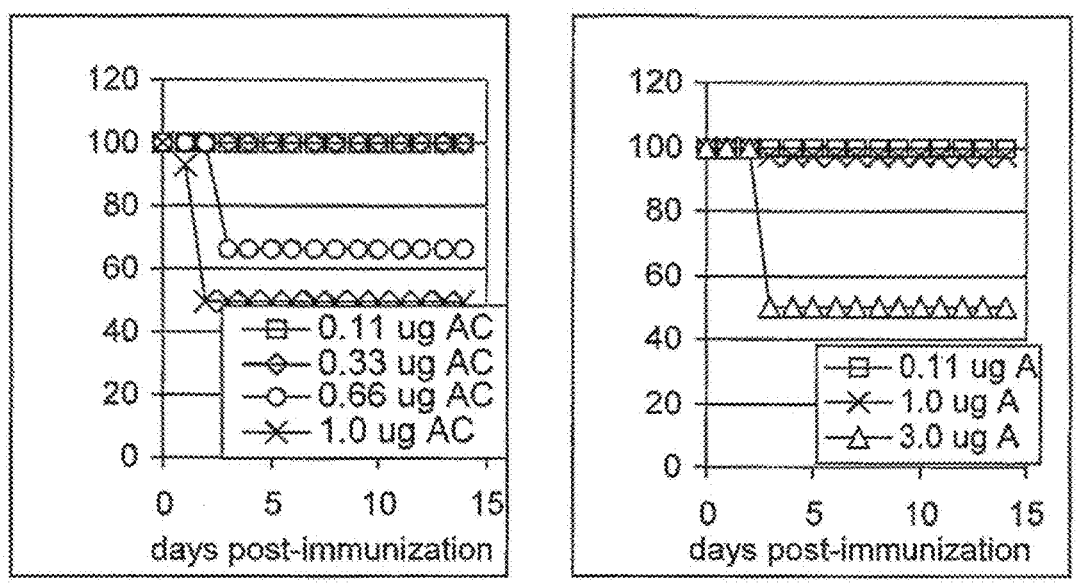

One litter of at least 7 newborn (one week old) mice per group were injected intraperitoneally (i.p.) once with either a formulation 703 iscoms or QWT iscoms The dose groups of each quillaja component ranged between 0.11 μg and 1 μg measured as protein content (FIG. 3). The weight ratio QWT or 703 (quillaja saponin) to protein is 1/1. The pups were observed for 15 days after i.p. injection. It should be noted, that the i.p. injection is a rough mode of administration and mice are much more sensitive for i.p. injection than for intramuscular and subcutaneous modes of administrations.

Results

Doses of 0.66 and 1 μg killed 65 resp. 50% oldie mice injected with the 703 iscoms, while all the mice injected with the QWT iscoms survived including those receiving 1 μg of QWT iscoms.

Conclusion

The QWT iscom is well tolerated even by a harsh route as the i.p. route in a very sensitive animal model. It is better tolerated than a formulation being in human trials.

Example 3

In this example the serum antibody response was tested with the envelope proteins G and F of hRSV as a model for vaccine antigen. The hRSV antigens were selected because hRSV represents antigens from a pathogen for which a vaccine is lacking and for which there is a great need. The newborn mouse represents a model for the newborns, which are immunologically immature requiring an adjuvant system with potent immune modulatory capacity (WO97/30727). Furthermore, a newborn mouse represents an animal system, which is very sensitive and requires a vaccine formulation virtually free of side effects. Similar vaccine formulations were tested as described in example 2, i.e. the QWT AND 703 iscoms.

Materials and Methods

Formulation of QWT and 703 RSV-Iscoms

See example 2

Experimental Design

One-week-old mice and adult mice (BALB/C) were distributed into 2 groups of newborns and 2 groups of adults. One litter of newborns with minimum of 7 animals per group and 8 adults were immunised i.p. with 1 µg of hRSV in the QWT iscoms or in the 703 iscom formulation. One group of newborns and 1 group of adult mice were immunised once, while 1 group of newborns and 1 group of adult mice were boosted 3 weeks after the first immunisation with the same formulations by the same mode. All experiments were repeated once.

Sera were collected before boost and week 7 of life i.e. 3 weeks after boost. Because of the small size of the newborns the sera were pooled from one group Antibody Determination The specific RSV serum antibody responses were determined by ELISA in both IgG1 and IgG2a subclasses as described using 0.1 µl of formalin killed RSV virus as coating antigen (Johansson. M and Lovgren-Bengtsson (1999) Iscoms with different quillaja saponin components differ in their immunomodulating activities. Vaccine 19, 2894-2900).

Results

Figure 4:
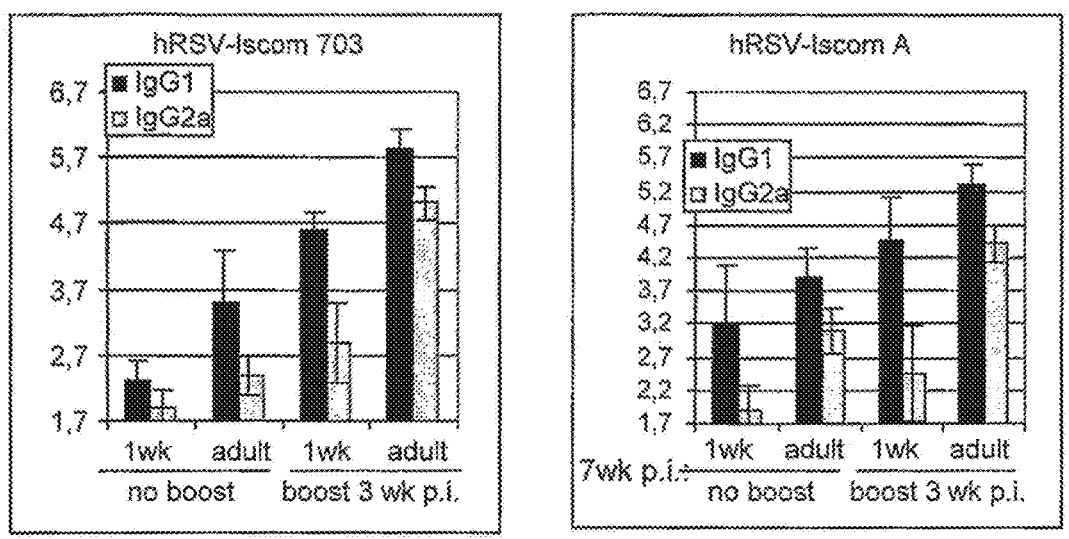

The results are illustrated in FIG. 4. After one immunisation both adults and newborns responded with RSV specific IgG1 antibodies measured by ELISA. After one immunisation the QWT iscoms induced higher RSV specific IgG1 antibody response in the newborn than the 703 iscom. Otherwise, there were no clear differences between the two iscom formulations as regards to their capacity to induce IgG1 and IgG2a RSV specific antibody responses in adults or in newborns. The antibody titres in general were 10-fold higher in the adults than in newborns. The IgG2a response to RSV was insignificant after one immunisation in newborns regardless they were immunised with QWT or 703 iscoms. RSV specific IgG2a were clearly detected after one immunisation in adults.

Conclusion

The serum antibody responses were at least as high after 1 as well as after 2 immunisations of newborns or adults with the QWT iscom formulation as after the same immunisation schedules with the 703 iscom. In view of the results of example 2, showing that the QWT iscom has a considerably lower toxicity than the 703 iscom, the QWT iscom is preferred for vaccine formulation.

Example 4

Cytotoxic T lymphocytes (CTL) are essential for the immune defence against intracellular pathogens. Above all virus-infected cells are targets for CTL by killing the infected cells. Consequently, CTL is an important arm of the immune defence against viral infections. This example shows that QWT iscoms containing hRSV envelope antigens specifically induce and efficiently prime for memory CTL both in newborn and adult mice. It is surprising, that the QWT iscoms induced CTL memory as efficiently in the newborns as in adults in view of their immature immune system.

Materials and Methods

Formulation of QWT and 703 RSV Iscoms

The QWT and 703 ISCOMs were prepared as described in example 2.

Animals and Experimental Design

Figure 5:
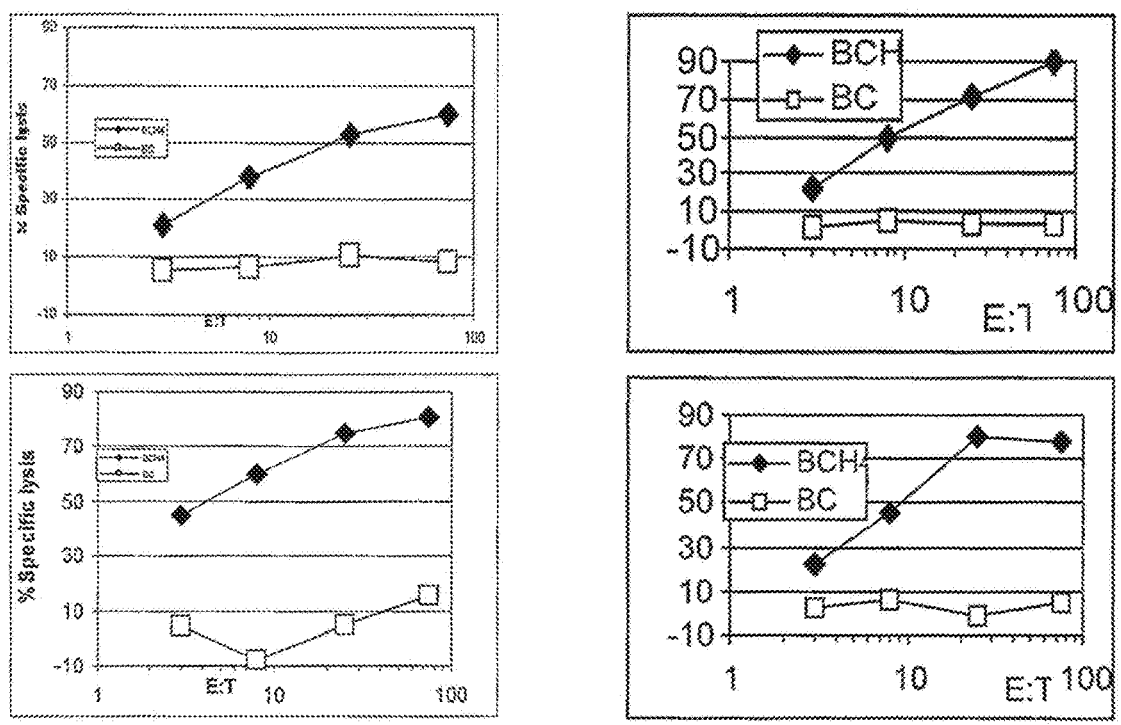

One litter of newborns with at least 7 animals were used for each experiment (8 adult BALB/C(H-2Kd) mice). Each experiment was carried out twice. One-week-old mice or adult mice were injected i.p. with 1 µg of QWT iscoms. One week resp. 3 weeks after immunisation spleen cells (effector cells) were cultured (restimulated) for 6 days in vitro with HRSV infected (BCH4)-fibroblast (target cells). The ratio of effector/target (E/T) ranged from 2 to 100 (FIG. 5). The target cell lysis was measured by Cr51 release and expressed as % specific lysis (% SL) according to standard procedure. 100% lysis was measured as Cr51 release from detergent treated cells. The background was the lysis caused by uninfected fibroblasts (BC) (see FIG. 5).

Results

Already 1 week after priming of newborn and adult mice with QWT iscoms their splenocytes generated to restimulation in vitro with hRSV infected fibroblasts (BCH4) strong cytotoxic T cell response (FIG. 5). No lysis was observed against uninfected target cells (BC in FIG. 5).

Conclusion

RSV-QWT iscoms induce strong cytotoxic T cell responses in 1-week-old mice and in adult mice. Strong specific cytotoxicity is observed already 1 week after one immunisation. In view of the strong adjuvant effect of QWT iscoms and its low toxicity, this vaccine delivery and adjuvant system is very likely to be valuable for both human and animal vaccines.

Example 5

Quillaja saponins have been shown to have strong adjuvant effects, but they have caused side effects by their lytic properties, which can be measured by lysis of red blood cells. Toxic effects of any kind prevent the cell growth or proliferation of living cells. It is well established that QHC and less purified quillaja saponins like Quil A lyses red blood cells (Ronnberg B, Fekadu M and Morein B, Adjuvant activity of non-toxic Quillaja saponaria Molina components for use in iscom matrix, Vaccine, 1995 13, (14): 1375-82). It is also clear that lytic effect of quillaja saponins causes local reactions when injected. One way to avoid lytic effects of saponins is to include them into ISCOM matrix. Furthermore, the side effects can be reduced by selection of quillaja saponin, which causes comparatively low side effect. In this example the effect of QWT matrix is tested on VERO cells, which is a primate cell line, and it is compared with QHC and 703 matrix formulations. In a second experiment spleen cells from mice were exposed to QWT and QHC matrices. The spleen cells are representative for the lymphatic system essential for the induction of immune responses. The AlamarBlue Assay is used, which measures quantitatively the proliferation of the cells based on detection of metabolic activity.

Materials and Methods

Cells and cell growth. Vero cells were cultured in RPMI 1640 medium (National Veterinary Institute Uppsala Sweden) supplemented with 7% fetal calf serum (obtained as above). After outgrowth on 75 $cm^2$ flasks (Corning-Costar, Acton Mass., USA) the cells are detached from the plastic surface and diluted to 25 to 30 000 per ml, and distributed in 100 µl portions per well in 96 well cell culture plates (Nunc A/S, Roskilde, Denmark). The cultures are incubated in CO₂ atmosphere for 24, 48 and 72 hours. Matrix prepared with QWT, or 703 or QHC were diluted in medium from 0 to 1300 µg per ml. The cell cultures were emptied from medium and the matrix dilutions were added to the wells. As control only medium was used. The test was carried out with the formulations to be tested for incubation periods of 24, 48 and 72 hours. Most suitable time period was 72 hours, which is presented here. The controls are considered as 100% growth.

Figure 6:
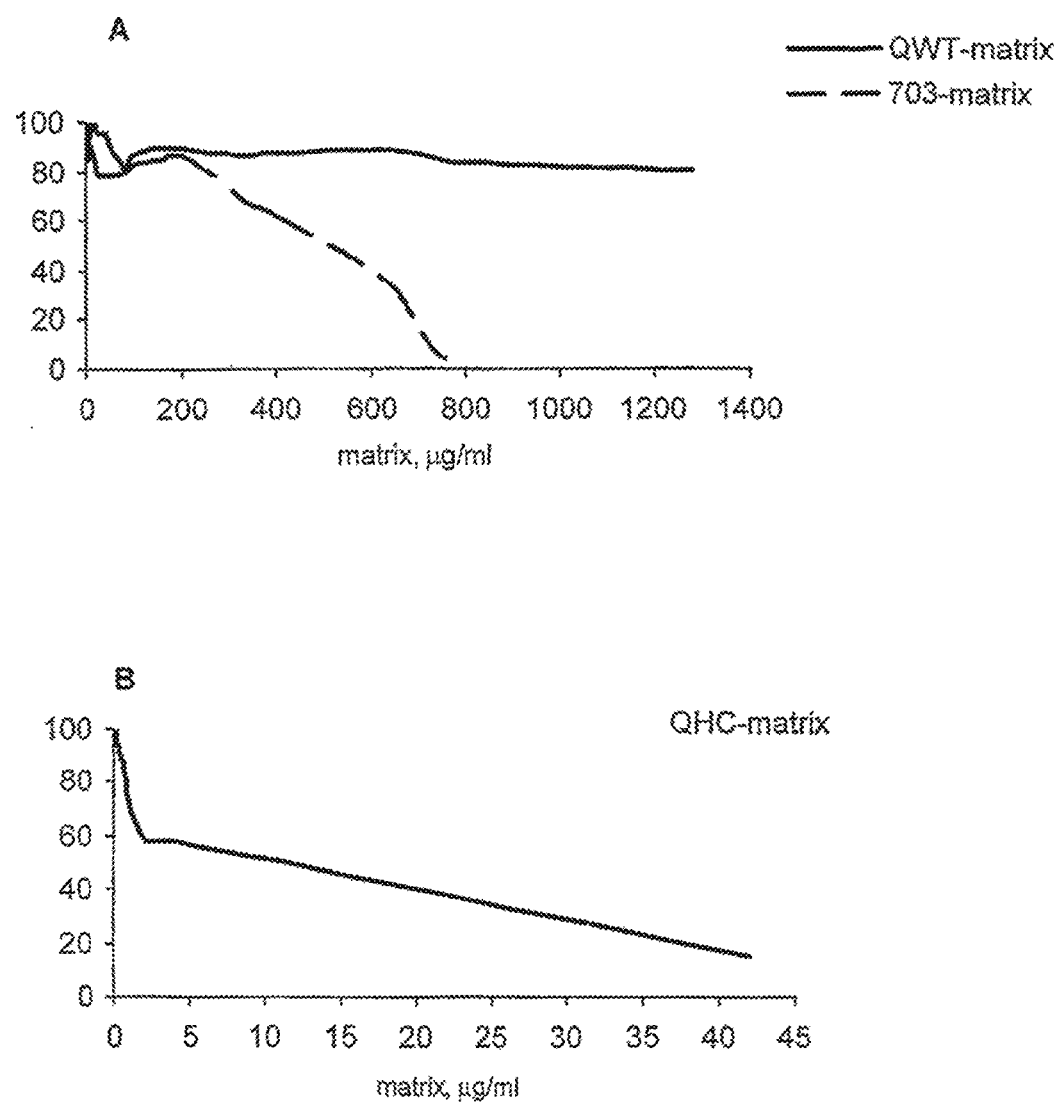

Recording of cell growth. The AlamarBlue assay (Serotec Ltd, Oxford UK), which measures quantitatively the proliferation of the cells based o detection of metabolic activity was used according to the description of the manufacturer.
Results After 72 hours incubation of the cell cultures with QWT matrix at a concentration 1300 µg per ml a cell growth of 80% was recorded compared to the control cultures, while the cell growth had declined to 0% when exposed to 703 matrix at a concentration of 800 µg per ml. The cell growth had declined to 0% when exposed to QHC matrix at concentration of 40 µg per ml. FIG. 6 illustrates one experiment out of 3 with similar results.
Conclusion QWT matrix is well tolerated by the cells and has very low cell toxic effect.

In a second experiment spleen cells were exposed to QWT and QHC matrices

Materials and Methods

Cells and cell growth. Spleen cells from Balb/C mice were cultured in RPMI 1640 medium (National Veterinary Institute, Uppsala, Sweden) supplemented with 7% fetal calf serum in 96-well cell culture plates (Nunc, Roskilde Denmark). The test was carried out on the spleen cells with the formulations QWT-iscom and QHC-iscom for incubation periods of 24, 48 and 72 hours. Most suitable period was 72 hours, which is presented here. The controls are considered as 100% growth.

Figure 7:
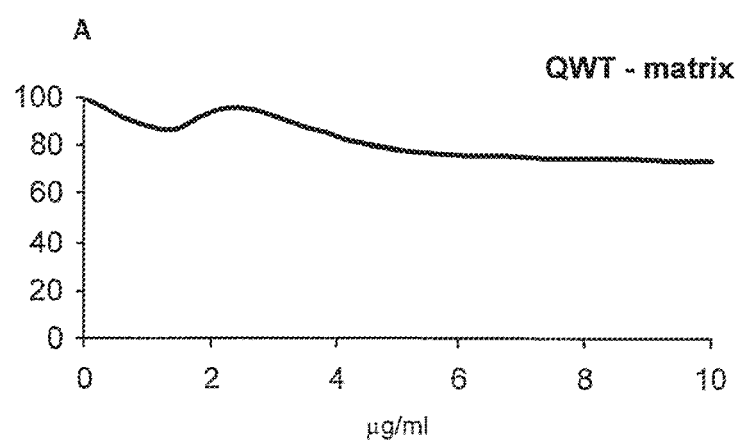
Figure 7:
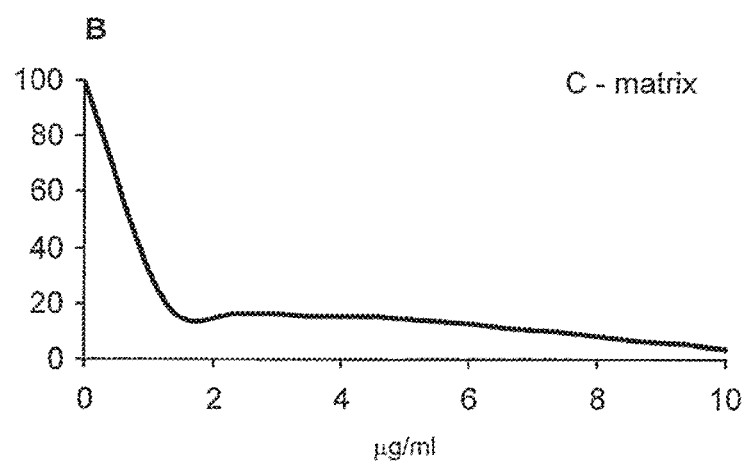
Figure 8:
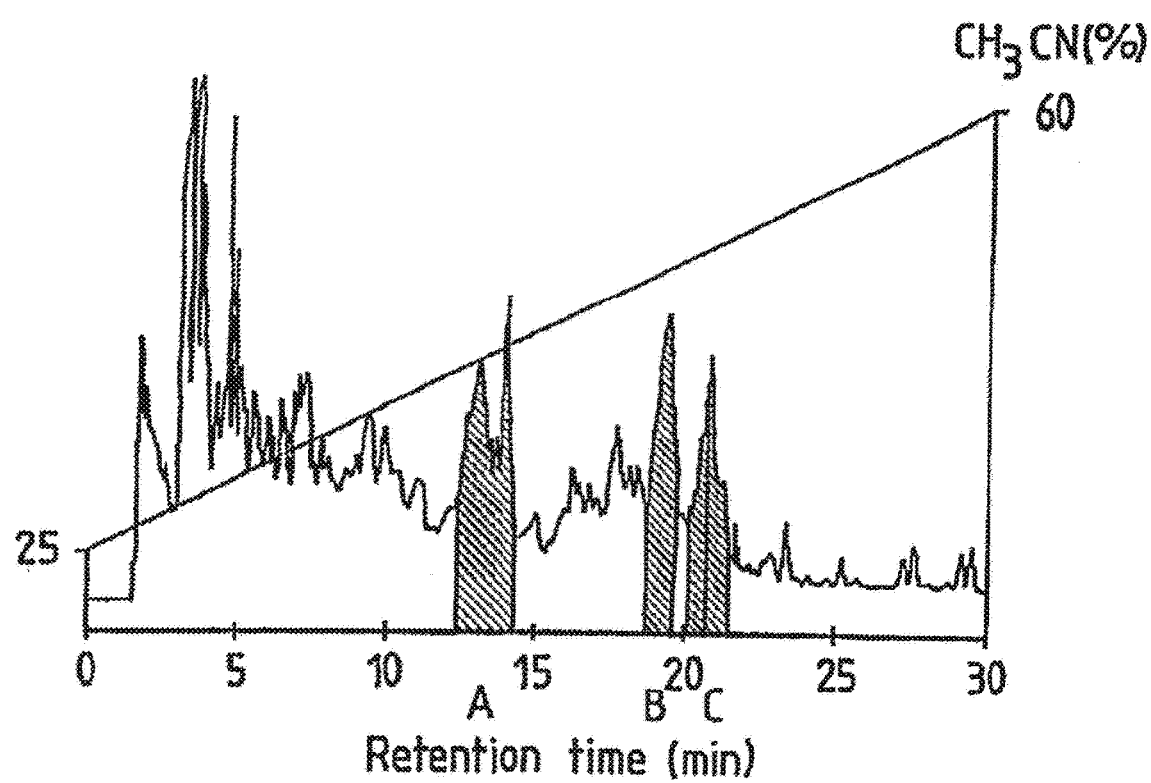

Recording of cell growth. The AlamarBlue Assay is used, which measures quantitatively the proliferation of the cells based on detection of metabolic activity was used according to the description of the manufacture.
Results After 72 hours exposure of the spleen cell cultures to QWT matrix at a concentration 10 µg per ml a cell growth of 80% was recorded compared to the non-exposed spleen cell (control) cultures, while the cell growth had declined close to 0/o when exposed to QVC matrix at a concentration of 2 µg per ml (FIGS. 7(A) and (B)). FIG. 7 illustrates one experiment out of 3 with similar results.

Example 5 Preparation of *Quillaja saponaria* Molina Subfragment Saponins

Purification of crude *Quillaja saponaria* Molina extract to fractions A, B and C. A solution (0.5 ml) of crude Quillaja bark extract in water (0.5 g/ml) is pre-treated on a sep-pak column (Waters Associates, Mass.).

The pre-treatment involves washing of the loaded sep-pak column with 10% acetonitrile in acidic water in order to remove hydrophilic substances. Lipophilic substances including QH-A, QH-B and QH-C are then eluted by 70% acetonitrile in water.

The lipophilic fraction from the sep-pak column is then separated by a semipreparative HPLC column (CT-sil, C8, 10.times.250 mm, ChromTech, Sweden).

The sample is eluted through the column by a gradient from 25% to 60% acetonitrile in acidic water. Three fractions are collected from the HPLC column during the separation. The residues after evaporation of these three fractions constitute QH-A, QH-B and QH-C.

The fractions designated QH-A, QH-B and QH-C were eluted at approximately 39, 47 and 49% acetonitrile respectively. The exact elution profile and conditions are shown in FIG.

Example 6

OVA is a weak antigen requiring adjuvant for induction of potent immune response. Prospective adjuvants are, therefore, often tested together with OVA to show the immune enhancement quantitatively by measuring level of antibody or qualitatively by measuring the immune modulatory effect. The modulatory effect is e.g. recorded by the capacity to drive antigen specific IgG subclass responses. A response dominated by IgG1 antibody is significant for Th2 while IgG2a is significant for Th1 type of response. A response in both IgG1 and IgG2a implicates the balance of the immune modulation between Th1 and Th2. This example it is carried out to demonstrate that QWT-Matrix acts synergistic with the more toxic QHC-Matrix to allow the use of a comparatively low and well tolerated dose of QHC-Matrix with optimized effect.

Materials and Methods

QWT and QHC-Matrix

These Quillaja saponin components (see Example 5) were obtained and formulated into ISCOM-Matrix as described in Example 1. Ovalbumin (OVA) was obtained from Sigma (St Louis, USA).
Experimental Design All mice were immunised s.c. at the base of the tail with a total volume of 100 µl. Group 1 consisted of 8 Balb/c mice immunised twice 4 weeks apart, with 5 µg OVA without addition of adjuvant. Group 2 consisted of 8 mice immunised twice 4 weeks apart, with 5 µg OVA adjuvanted with 6 µg QWT-Matrix. Group 3 consisted of 8 mice immunised twice 4 weeks apart with 5 µg OVA adjuvanted with 6 µg QHC-Matrix. Group 4 consisted of 8 mice immunised twice 4 weeks apart with 5 µg OVA adjuvanted with low dose of QHC-Matrix (2 µg) supplemented and supplemented with 6 µg QWT-Matrix.

Sera were collected before first immunisation and 3 weeks after priming and 2 weeks after the boost
Antibody Determination Serum antibody determination, including total IgG, and subclasses IgG1 and IgG2a, was carried in out in ELISA as described in example 1.
Results After priming (FIG. 9), there was an IgG response over 1.100 in 1 out of 8 mice immunised with OVA+QWT-Matrix (group 2), in 2 out of 8 mice in the group immunised with OVA+QHC-matrix (Group 3). In contrast all 8 mice in the group immunised with low dose of QHC-matrix complemented with QWT-Matrix (Group 4) responded with an IgG response. None of the mice immunised with OVA alone responded with a titre >1:100 after the primary immunisation.

After priming 2 out of 8 mice in the group immunised with the combination of QWT-Matrix Matrix and a low dose of QHC-matrix (Group 4) responded with an antigen specific IgG2a response >1:100. No IgG2a response was recorded after priming in the other groups.

Figure 10:
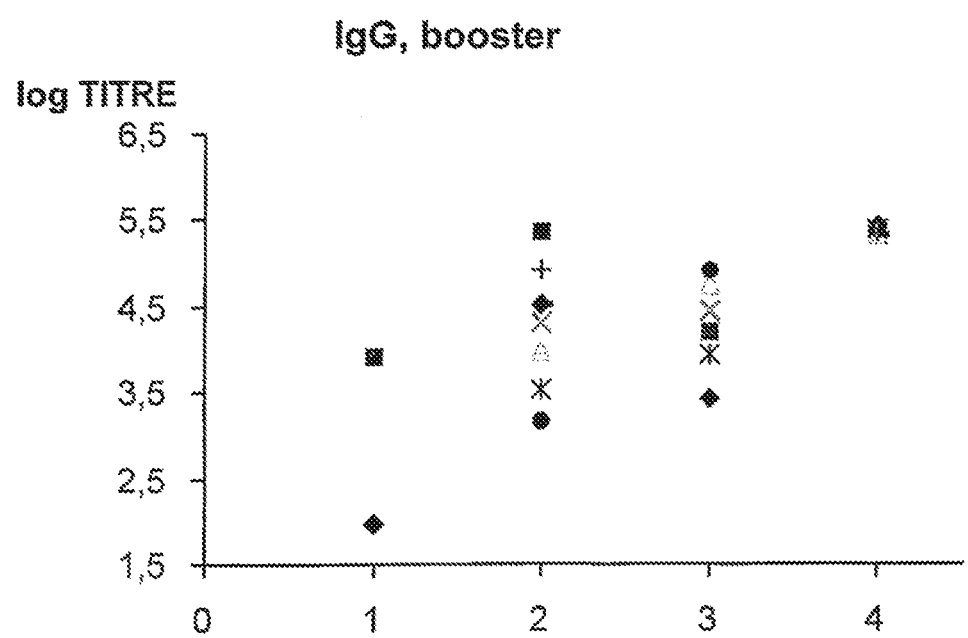
Figure 11:
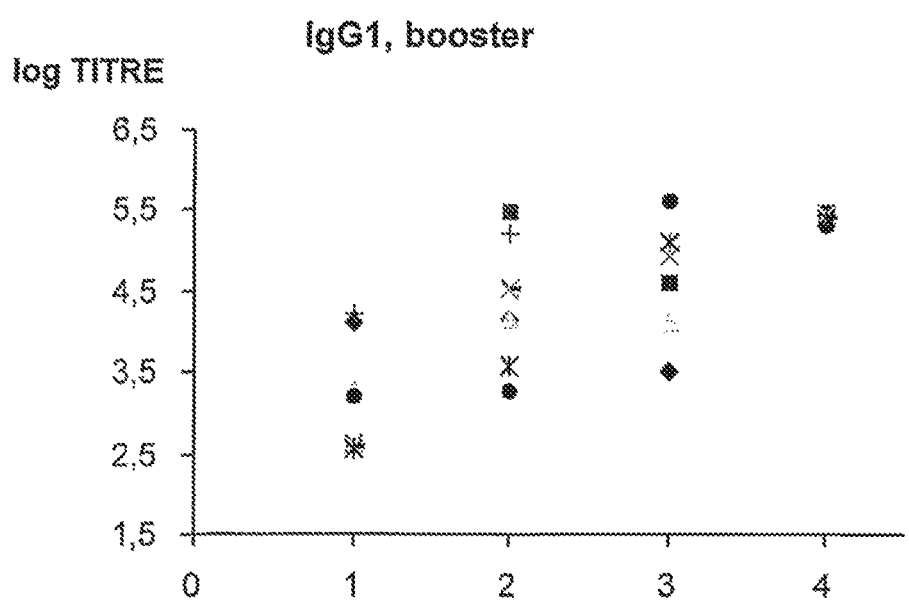
Figure 12:
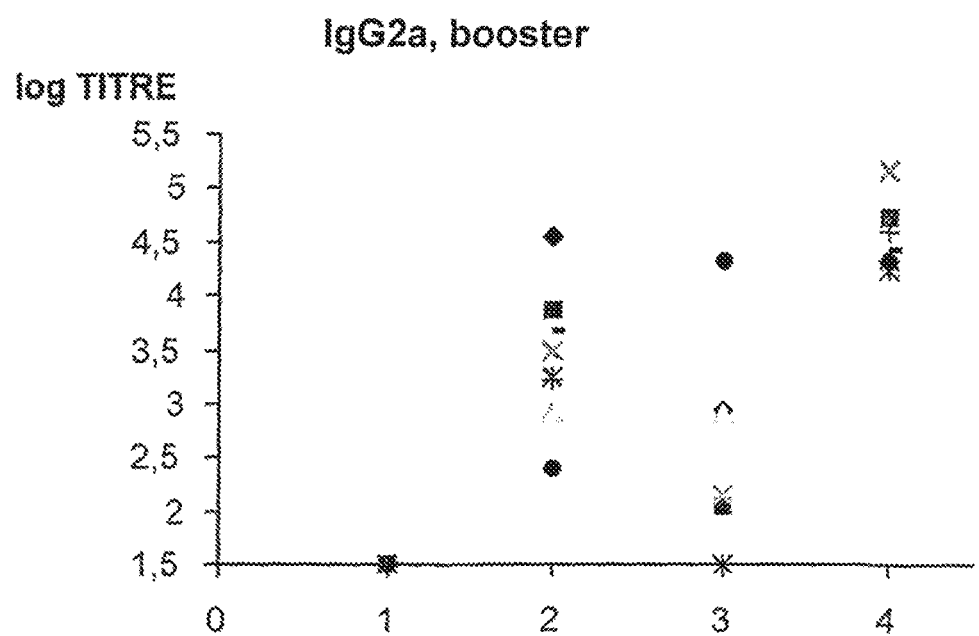

After booster (FIG. 10, FIG. 11, and FIG. 12), all mice in groups 2, 3 and 4 responded with IgG tires >1:100. However, the titres in Group 2 and Group 3 varied over 2 logs (3 700-295 000 and 3 100-400 000 respectively), while the titres in group 4 varied within 1/10 of a log (260 000-350 000).

The IgG1 results after priming were mirrored by that of the IgG (total) response. Thus, these results are not depicted by a figure.

The antigen specific IgG2a response after booster was negligible in Group 2 given OVA+WAIT-Matrix. Groups 1 and 3 showed variable responses of the IgG2a subclass while in Group 4, given OVA+QWT-Matrix and 2 µg of QHC-matrix all responded with high IgG2a titres, all within one log Conclusion QWT-Matrix in a low dose is well tolerated and without measurable side effects in the dose used in this example, but it is also tolerated in a many-fold higher dose as shown in example 1. In this example QHC-Matrix was used in a low and well tolerated but sub-optimal dose for adjuvant use by its own. It is clearly documented in this experiment, that QWT-Matrix and QHC-Matrix acts synergistically in a well tolerated adjuvant formulation. It should be emphasised that both the QWT-Matrix and QHC-Matrix doses, as used in the combined formulation in this example, are too low to be effective by their own, implicating synergism.

Example 7

In this experiment the synergistic effect of QWT-Matrix is tested on potent adjuvant active bacterial derived compounds; mono phosphoryl lipid A (MPL) and cholera toxin (CT). It is evaluated with regard to enhancement of the immunogenicity of the week antigen, OVA. The NMRI out-bred mice were used, which in contrast Balb/C mice readily respond with TH1 as well as TH2 type of immunity reflected by the IgG2a (Th1) and IgG1 (Th2) antibody levels.

Materials and Methods

OVA QWT-Iscoms

These ISCOMs were prepared essentially as described for QWT-Matrix in example 1, with the exception that palmitified OVA (pOVA) was added to the preparation at a concentration of 1 mg per mg cholesterol. The preparation of pOVA-iscoms have been described by Johansson and Lövgren-Bengtsson in Vaccine 17 (1999), p 2894. CT was commercially obtained from KeLab, Gothenburg, Sweden. MPL (L6895) and OVA were from Sigma (St. Louis, USA).

Experimental Design

All mice were immunised s.c. at the base of the tail with a total volume of 100 Group 1 consisted of 8 NMRI mice immunised twice, 4 weeks apart with 5 µg OVA without addition of adjuvant. Group 2 consisted of 8 mice immunised twice 4 weeks apart with 5 µg OVA incorporated into QWT-iscoms containing bug QWT and no additional adjuvant. Group 3 consisted of 8 mice immunised twice 4 weeks apart with 5 µg OVA (as in group 1) adjuvanted with high dose CT (1 µg). Group 4 consisted of 8 mice immunised twice 4 weeks apart with 5 µg OVA (as in group 1) adjuvanted with high dose of MPL (50 µg). Group 5 consisted of 8 mice immunised with 5 µg OVA in QWT-ISCOMs (as in Group 2) supplemented with low dose (0.2 µg) CT. Group 6 consisted of 8 mice immunised twice 4 weeks apart with 5 µg OVA in QWT-iscoms (as in Group 2) adjuvanted with low dose (10 µg) MPL.

Sera were collected 3 weeks after priming and 2 weeks after the booster injection.

Antibody Determination

Serum antibody determination, including total IgG, and subclasses IgG1 and IgG2a, was carried in out in ELISA as described in example 1.

Results

Figure 13:
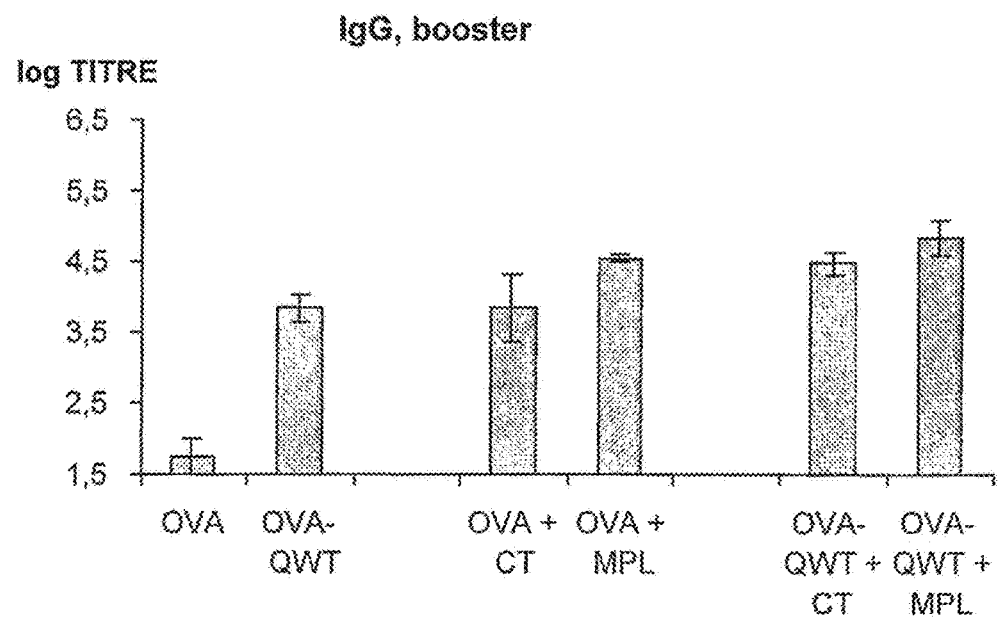
Figure 13:
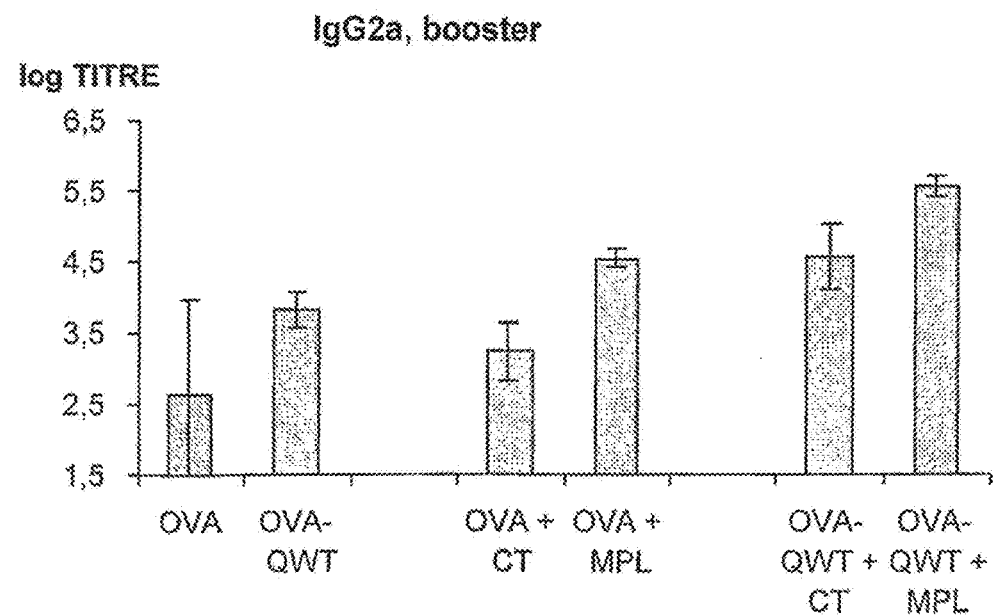

The results are depicted in FIG. 13.

After the first immunisation the total IgG levels were comparable for groups 2 to 6 and IgG2a antibody response to OVA was low for mice in all groups (not shown).

After booster (FIG. 13(A)) the mice immunised with OVA alone reacted with low serum levels of IgG. The OVA in QWT-ISCOM supplemented with low dose of CT (0.2 µg) induced 7-fold higher IgG levels than the OVA adjuvanted with high dose (1 µg) of CT. The OVA in QWT-ISCOM supplemented with low dose of MPL (10 µg) induced 2 fold higher IgG levels than the OVA adjuvanted with high dose (50 µg) of MPL.

The IgG1 were essentially reflected by the total IgG antibody responses, and are not shown.

Greater differences were recorded when measuring the antibody responses within the IgG2a subclass (FIG. 13(B)). The MPL low dose was enhanced about 10-fold in IgG2a serum antibody levels with OVA in QWT-ISCOM formulation compared to OVA adjuvanted with the high dose of MPL. Even more striking is the 100-fold enhancement of the IgG2a response by the OVA-QWT-ISCOM with low dose CT compared to OVA formulated with a high dose CT.

Conclusion

OVA in QWT-ISCOM formulated with low dose of CT or MPL were considerably more immunogenic than the corresponding MPL or CT high doses formulations excluding QWT. The QWT-ISCOM enhancement of the immunogenicity of OVA was most striking in the IgG2a subclass showing strong immune modulatory effects of the QWT component in the respective formulations. Although the Th1 modulation was more striking than that of Th2, the modulation geared by QWT-ISCOM was balanced. The Th1 driving effect was more prominent over CT explained by the fact that CT is more Th2 driving than MPL.

Example 8

Vaccines are often composed of antigens in particulate forms as is often the case with vaccines against bacteria or viruses. Toxins on the other hand are soluble antigens detoxified by conversion to toxoids e.g. by treatment with formalin. In example 1 (FIG. 2) and in examples 6 and 7 it is shown that the immunogenicity of a weak soluble antigen OVA is strongly enhanced by the synergistic effect of QWT-Matrix, when the QWT-Matrix is used to complement a low and well tolerated dose of QHC-Matrix, CT or MPL.

In this example a commercial soluble but immunogenic vaccine antigen, Tetanus Toxoid (TT) is supplemented with Cholera Toxin (CT) being a strong adjuvant driving a Th2 type of response, but also toxic in comparatively low doses. Included in the example is also a group of mice immunised with TT and adjuvanted with CT complemented with QWT-Matrix. QWT-Matrix is added to show that modulation of the CT response can be achieved with a low dose of CT and that a well tolerated CT/QWT formulation can be obtained, which is well tolerated due to a synergistic effect.

Materials and Methods

Figure 17:
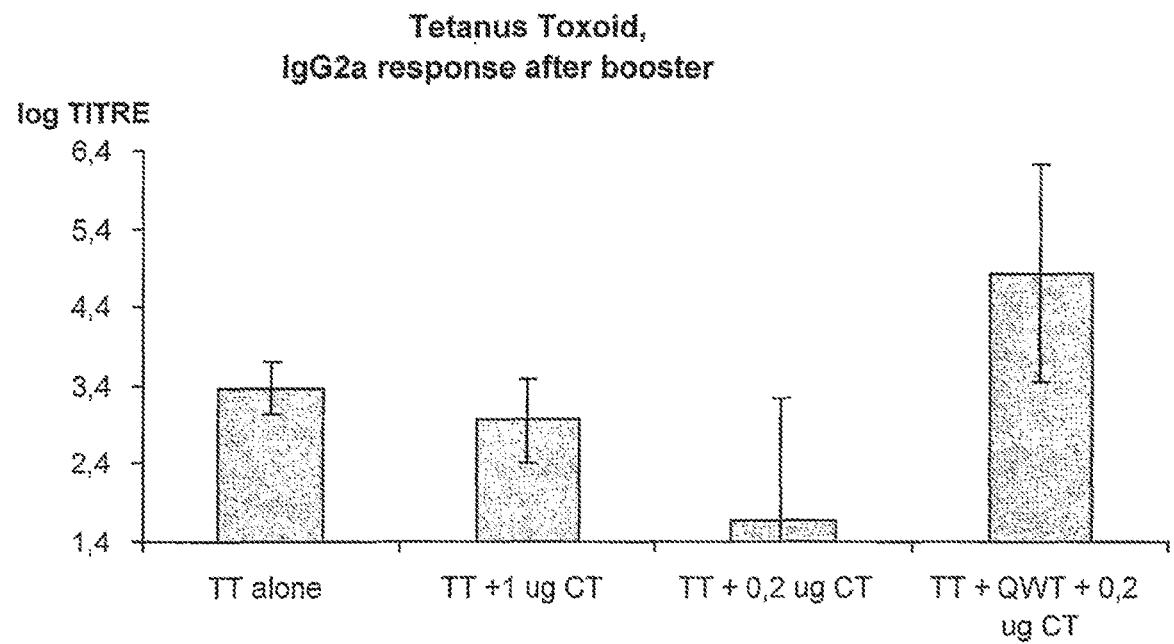

QWT-Matrix
QWT-Matrix was formulated as described in Example 1.
TT and CT
TT was commercially obtained from The State SERUM Institute, Copenhagen, Denmark.
CT was commercially obtained from KeLab, Gothenburg, Sweden.
Experimental Design
All mice were immunised s.c. at the base of the tail with 100 μl of vaccine. Group 1 consisted of 6 outbred NMRI mice immunised twice 4 weeks apart with 2.5 Lf TT without addition of adjuvant. Group 2 consisted of 8 mice immunised twice 4 weeks apart with 2.5 Lf TT adjuvanted with high dose of CT (1 μg). Group 3 consisted of 8 mice immunised twice 4 weeks apart with 2.5 Lf TT adjuvanted with low dose of CT (0.2 μg). Group 4 consisted of 8 mice immunised twice 4 weeks apart with 2.5 Lf TT adjuvanted with low dose of CT (0.2 μg) supplemented with 10 μg of QWT-Matrix.
Sera were collected 3 weeks after the priming and 2 weeks after the booster.
Antibody Determination
This was carried in out in ELISA as described in example 1 except that the antigen was TT coated to ELISA plates (Nunc) at a concentration of 1 μg/ml.
Results
A clearcut primary antibody response, measured as antigen-specific IgG, was recorded in all four groups showing that TT is a comparatively strong immunogen. TT adjuvanted with low dose of CT (0.2 μg) supplemented with QWT-Matrix induced a 3-fold higher primary IgG response compared to the other formulations (FIG. 14).
After booster, the total IgG response increased in all groups where the TT was supplemented with adjuvant (FIG. 15), while the second immunisation did not significantly increase the antibody level in mice immunised with TT alone.
After one immunisation the IgG2a response, indicating a Th1 type of immune response, was only induced in mice (group 4) immunised with TT adjuvanted with low dose of CT (0.2 μg) supplemented with QWT-Matrix (FIG. 16).
After booster, the QWT-Matrix group of mice responded with the highest IgG2a titres (FIG. 17). Mice in group 3 immunised with TT adjuvanted with the low dose of CT (0.2 μg) dose responded with negligible or very low titres of TT-specific IgG2 antibody
Conclusion
TT is a comparatively strong soluble immunogen promoting a Th2 type of response. CT is a strong toxin with strong adjuvant effect also promoting a Th2 type of response. In this experiment it is shown that QWT-Matrix strongly promotes (modulates) the host to respond also with antigen-specific IgG2a antibody when added to the TT antigen supplemented with low dose of CT. It is interesting to note the strong Th2 driving adjuvant effect of CT is modulated by QWT-Matrix towards Th1. Thus, the QWT-Matrix has a strong immune modulatory effect combined with CT as adjuvant.

Example 9

In this example a commercial soluble vaccine antigen Tetanus Toxoid (TT) is supplemented with monophosphoryl lipid A (MPL) being a strong adjuvant driving a Th1 type of response. A low dose of MPL was complemented with QWT-Matrix to demonstrate the modulatory and synergistic effect of QWT-Matrix on the TT antigen in the presence of MPL.

Materials and Methods

Figure 21:
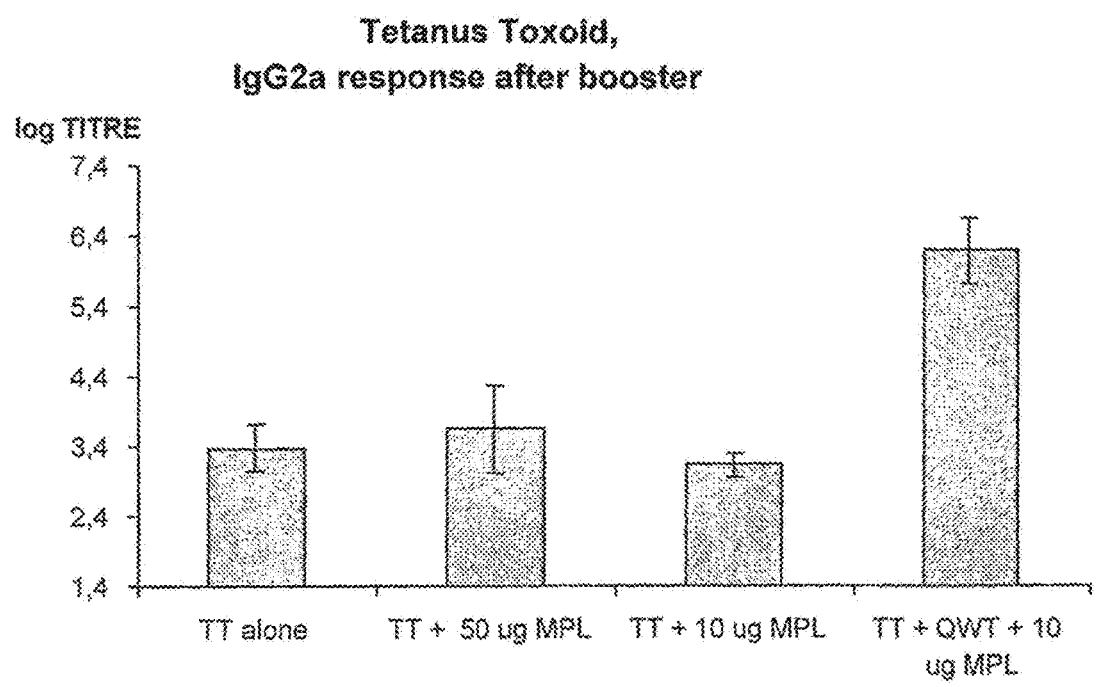

QWT-Matrix
QWT-Matrix was formulated as described in Example 1.
TT and MPL
TT was commercially obtained from The State SERUM Institute, Copenhagen, Denmark.
MPL (L6895) was from Sigma (St. Louis, USA)
Tetanus Toxoid (TT)
TT was commercially obtained from The State SERUM Institute, Copenhagen, Denmark.
Experimental Design
All mice were immunised s.c. at the base of the tail with 100 μl of vaccine. Group 1 consisted of 6 outbred NMRI mice immunised twice 4 weeks apart with 2.5 Lf TT without addition of adjuvant. Group 2 consisted of 8 mice immunised twice 4 weeks apart with 2.5 Lf TT adjuvanted with high dose of MPL (50 μg). Group 3 consisted of 8 mice immunised twice 4 weeks apart with 2.5 Lf TT adjuvanted with low dose of MPL (10 μg). Group 4 consisted of 8 mice immunised twice 4 weeks apart with 2.5 Lf IT adjuvanted with low dose of MPL (10 μg) supplemented with 10 μg of QWT-Matrix.
Sera were collected 3 weeks after the priming and 2 weeks after the booster.
Antibody Determination
This was carried out as described in example 8.
Results
A clearcut primary antibody response, measured as antigen-specific IgG, was recorded in all four groups showing that TT is a comparatively strong immunogen (FIG. 18). TT adjuvanted with low dose of MPL (10 μg) supplemented with QWT-Matrix induced about 2-fold higher primary IgG response than the formulation TT adjuvanted with 10 μg MPL.
After booster the total IgG antibody response was substantially increased in all groups where the TT was supplemented with adjuvant (FIG. 21), while the second immunisation did not significantly increase the antibody level in mice immunised with TT alone. The mice immunised with TT adjuvanted with MPL (10 μg) supplemented with QWT-Matrix responded with more than a 100 fold specific IgG response (FIG. 19), which was about 8-fold higher than the response induced by TT supplemented low dose of MPL (10 μg), but no QWT-Matrix.
The IgG1 response showed the same profile as the total IgG response both after the primary and second immunisation.
Mice immunised TT adjuvanted low dose of MPL (10 μg) supplemented with QWT-Matrix responded with 10 fold higher IgG2a titres than mice immunised with TT supplemented with low dose of MPL (FIG. 20). Mice in other groups did not develop significant primary IgG2a response.
After booster the mice immunised with TT adjuvanted with low dose of MPL (10 μg) supplemented with QWT-Matrix responded with the highest IgG2a titres being more than 100-fold higher than mice in other groups (FIG. 21).
Conclusion
QWT-Matrix with antigen and/or MPL potently enhanced IgG2a antibody response, but also IgG1 indicating a strong balanced immune modulatory effect on the TT antigen in the presence of MPL. The strong immunogenicity of TT is emphasised by the fact that MPL by its own did not or only marginally enhance the total IgG or IgG2a or IgG1 responses to the TT antigen. This indicates that a strong adjuvant, like MPL, might have a limited immune modulatory effect in the presence of a strong immunogen like TT. In contrast, QWT is symbiotic in the effect with MPL demonstrated by the fact that this combination has a strong immunomodulatory effect.

The invention claimed is:

1. A method of enhancement of an immune response level and an immunomodulating activity comprising administering to a human subject an effective amount of an adjuvant composition with synergistic effect of low toxicity comprising
   (i) immunostimulating complex (ISCOM) particles comprising a saponin fraction consisting essentially of fraction A of Quil A, and
   (ii) at least one other adjuvant,
   wherein the composition comprises 2-99.9% of fraction A of Quil based on the total weight of the composition;
   the ISCOM particles comprising the saponin fraction consisting essentially of fraction A of Quil A are less toxic on VERO cells than are QH703 ISCOM matrix particles;
   the at least one other adjuvant is in free form or integrated into ISCOM particles other than the ISCOM particles comprising the saponin fraction consisting essentially of fraction A of Quil A.

2. The method according to claim 1 wherein the at least one other adjuvant is chosen from the group consisting of: saponins, naturally occurring saponin molecules derived from crude saponin extract of *Quillaja saponaria* Molina, synthetic saponin molecules derived from crude saponin extract of *Quillaja saponaria* Molina, semisynthetic saponin molecules derived from crude saponin extract of *Quillaja saponaria* Molina, a saponin fraction of Quil A, saponin fractions from cell wall skeleton, block polymers, hydrophilic block copolymers, CRL-1005, Threhalose di mucolate (TDM), lipopeptides, LPS and LPS-derivatives, Lipid A from a bacterial species and derivatives thereof, monophosphoryl lipid A, CpG variants, CpGODN variants, endogenous human animal immunomodulators, GM-CSF, IL-2, native adjuvant active bacterial toxins, modified adjuvant active bacterial toxins, cholera toxin CT, CT subcomponent CTB, CT subcomponent CTA1, thermolabile toxin (LT) of *E. coli*, *Bordetella pertussis* (BP) toxin, and a filamentus heamagglutenin of BP.

3. The method according to claim 2 wherein the saponin fraction of Quil A is fraction C of Quil A or fraction B of Quil A.

4. The method according to claim 1, wherein the at least one other adjuvant is integrated into ISCOM particles other than the ISCOM particles comprising the saponin fraction consisting essentially of fraction A of Quil A.

5. The method according to claim 1, wherein the at least one other adjuvant is integrated into ISCOM particles other than the ISCOM particles comprising the saponin fraction consisting essentially of fraction A of Quil A and is not integrated into the ISCOM particles comprising the saponin fraction consisting essentially of fraction A of Quil A.

6. The method according to claim 1, wherein the at least one other adjuvant is not integrated into ISCOM particles.

7. The method according to claim 6, wherein the at least one other adjuvant is at least one of monophosphoryl lipid A and cholera toxin CT.

8. The method according to claim 1, wherein the ISCOM particles comprising the saponin fraction consisting essentially of fraction A of Quil A are ISCOM matrix particles.

9. The method according to claim 1, wherein the ISCOM particles comprising the saponin fraction consisting essentially of fraction A of Quil A further comprise at least one antigen substance.

10. The method according to claim 3, wherein the composition comprises
    50-99.9% of fraction A of Quil A; and
    0.1-50% of the saponin fraction of Quil A based on the total weight of the composition.

11. The method according to claim 3, wherein the composition comprises
    75-99.9% of fraction A of Quil A; and
    0.1-25% of the saponin fraction of Quil A based on the total weight of the composition.

12. The method according to claim 3, wherein the composition comprises
    91-99.1% of fraction A of Quil A; and
    0.1-9% of the saponin fraction of Quil A based on the total weight of the composition.

13. The method according to claim 1, wherein the composition further comprises a pharmaceutically acceptable carrier, diluent, excipient, or additive.

14. The method according to claim 1, wherein the immune response is an IgG response.

15. The method according to claim 1, wherein the immune response is a Th1 response.

16. The method according to claim 1, wherein the immune response is a Th2 response.

17. The method according to claim 1, wherein the immunomodulating activity is a Th1-Th2 balance.

* * * * *